US009718859B2

(12) United States Patent
Eldar-Finkelman et al.

(10) Patent No.: US 9,718,859 B2
(45) Date of Patent: Aug. 1, 2017

(54) GLYCOGEN SYNTHASE KINASE-3 INHIBITORS

(71) Applicants: Ramot at Tel-Aviv University Ltd., Tel-Aviv (IL); Yeda Research and Development Co. Ltd., Rehovot (IL)

(72) Inventors: Hagit Eldar-Finkelman, Shoham (IL); Miriam Eisenstein, Rehovot (IL); Avital Licht-Murava, Tel-Aviv (IL)

(73) Assignees: Ramot at Tel-Aviv University Ltd., Tel-Aviv (IL); Yeda Research and Development Co. Ltd., Rehovot (IL)

(*) Notice: Subject to any disclaimer, the term of this patent is extended or adjusted under 35 U.S.C. 154(b) by 0 days.

(21) Appl. No.: 14/392,205

(22) PCT Filed: Jun. 24, 2014

(86) PCT No.: PCT/IL2014/050567
§ 371 (c)(1),
(2) Date: Dec. 23, 2015

(87) PCT Pub. No.: WO2014/207743
PCT Pub. Date: Dec. 31, 2014

(65) Prior Publication Data
US 2016/0200763 A1 Jul. 14, 2016

Related U.S. Application Data

(60) Provisional application No. 61/838,347, filed on Jun. 24, 2013.

(51) Int. Cl.
*A61K 38/08* (2006.01)
*A61K 38/10* (2006.01)
*C07K 7/06* (2006.01)
*C07K 7/08* (2006.01)
*A61K 47/48* (2006.01)
*C40B 30/02* (2006.01)
*G06F 19/16* (2011.01)
*A61K 38/00* (2006.01)

(52) U.S. Cl.
CPC .............. *C07K 7/06* (2013.01); *A61K 38/08* (2013.01); *A61K 38/10* (2013.01); *A61K 47/48038* (2013.01); *C07K 7/08* (2013.01); *C40B 30/02* (2013.01); *G06F 19/16* (2013.01); *A61K 38/00* (2013.01)

(58) Field of Classification Search
CPC .. A61K 38/08; A61K 38/10; A61K 47/48038; C07K 7/06; C07K 7/08
See application file for complete search history.

(56) References Cited

U.S. PATENT DOCUMENTS

| 6,780,625 B2 | 8/2004 | Eldar-Finkelman |
| 7,378,432 B2 | 5/2008 | Eldar-Finkelman et al. |
| 2005/0164324 A1* | 7/2005 | Gygi ................. G01N 33/6842 435/23 |

FOREIGN PATENT DOCUMENTS

| WO | WO 01/49709 | 7/2001 |
| WO | WO 2004/052404 | 6/2004 |
| WO | WO 2004/108948 | 12/2004 |
| WO | WO 2005/000192 | 1/2005 |
| WO | WO 2005/012329 | 2/2005 |
| WO | WO 2011/149909 | 12/2011 |
| WO | WO 2012/101599 | 8/2012 |
| WO | WO 2012/101601 | 8/2012 |
| WO | WO 2014/207743 | 12/2014 |

OTHER PUBLICATIONS

Communication Relating to the Results of the Partial International Search Dated Oct. 9, 2014 From the International Searching Authority Re. Application No. PCT/IL2014/050567.
International Preliminary Report on Patentability Dated Jan. 7, 2016 From the International Bureau of WIPO Re. Application No. PCT/IL2014/050567.
International Search Report and the Written Opinion Dated Feb. 10, 2015 From the International Searching Authority Re. Application No. PCT/IL2014/050567.
Bertrand et al. "Structural Characterization of the GSK-3 [Beta] Active Site Using Selective and Non-Selective ATP-Mimetic Inhibitors", The Journal of Molecular Biology, 333: 393-407, 2003.
Chen et al. "Glycogen Synthase Kinase 3Beta (GSK3Beta) Mediates 6-Hydroxydopamine-Induced Neuronal Death", The FASEB Journal, p. 1-26, May 7, 2004.
Dajani et al. "Crystal Stricture of Glycogen Synthase Kinase 3 [Beta]: Structural Basis for Phosphate-Primed Substrate Specificity and Auloinhibilion", Cell, 105: 721-732, 2001.
Fiol et al. "Formation of Protein Kinase Regognition Sites by Covalent Modification of Substrate. Molecular Mechanism for the Synergistic Action of Casein Kinase II and Glycogen Synthase Kinase 3", The Journal of Biological Chemistry, 262(29): 14042-14048, 1987.
Ilouz et al. "Identification of Novel Glycogen Synthase Kinase-3[Beta] Substrate-Interacting Residues Suggests a Common Mechanism for Substrate Recognition", The Journal of Biological Chemistry, 281(41): 30621-30630, Oct. 13, 2006.

(Continued)

*Primary Examiner* — Jeffrey E Russel

(57) ABSTRACT

Novel peptide inhibitors of GSK-3, compositions containing same and uses thereof are disclosed. The novel peptide inhibitors are converted to inhibitors of GSK-3 upon interacting with the enzyme's catalytic site and hence act as disease-selective inhibitors for treating conditions associated with increased activity and/or expression of GSK-3. Each of the disclosed peptides is independently of no more than 15 amino acid residues, and has an amino acid sequence which comprises a $ZX_1X_2X_3Z(p)$ recognition motif of GSK-3, wherein $Z(p)$ is a phosphorylated serine or threonine residue; Z is a phosphorylatable serine or threonine residue, and each of $X_1$, $X_2$ and $X_3$ is independently any amino acid, as defined in the specification. Further disclosed are methods of identifying a putative substrate-competitive peptide inhibitor of GSK-3 which are effected by computational modeling and screening.

28 Claims, 5 Drawing Sheets
(4 of 5 Drawing Sheet(s) Filed in Color)

(56) References Cited

OTHER PUBLICATIONS

Kaidanovich-Beilin et al. "Long-Term Treatment With Novel Glycogen Synthase Kinase-3 Inhibitor Improves Glucose Homeostasis in Ob/Ob Mice: Molecular Characterization in Liver and Muscle", The Journal of Pharmacology and Experimental Therapeutics, 316(1): 17-24, 2006.
Kaidanovich-Beilin et al. "Rapid Antidepressive-Like Activity of Specific Glycogen Synthase Kinase-3 Inhibitor and Its Effect on Beta-Catenin in Mouse Hippocampus", Biological Psychiatry, 55: 781-784, 2004.
Kim et al. "Essential Roles for GSK-3s and GSK-3-Primed Substrates in Neurotrophin-Induced and Hippocampal Axon Growth", Neuron, 52: 981-996, Dec. 21, 2006.
Liberman et al. "Coordinated Phosphorylation of Insulin Receptor Substrate-1 by Glycogen Synthase Kinase-3 and Protein Kinase CBetaII in the Diabetic Fat Tissue", American Journal of Physiology. Endocrinology and Metabolism, 294(6): E1169-E1177, Jun. 2008.
Liberman et al. "Serine 332 Phosphorylation of Insulin Receptor Substrate-1 by Glycogen Synthase Kinase-3 Attenuates Insulin Signaling", The Journal of Biological Chemistry, 280(6): 4422-4428, Feb. 11, 2005.
Licht-Murava et al. "Elucidating Substrate and Inhibitor Binding Sites on the Surface of GSK-3[Beta] and the Refinement of a Competitive Inhibitor", Journal of Molecular Biology, 408: 366-378, 2011.
Palomo et al. "5-Imino-1,2,4-Thiadiazoles: First Small Molecules as Substrate Competitive Inhibitors of Glycogen Synthase Kinase 3", Journal of Medicinal Chemistry, 55(4): 1645-1661, Jan. 18, 2012.
Plotkin et al. "Insulin Mimetic Action of Synthetic Phosphorylated Peptide Inhibitors of Glycogen Synthase Kinase-3", The Journal of Pharmacology and Experimental Therapeutics, 305(3): 974-980, 2003.
Rao et al. "Glycogen Synthase Kinase 3 Inhibition Improves Insulin-Stimulated Glucose Metabolism But Not Hypertension in High-Fat-Fed C57BL/6J Mice", Diabetologia, 50: 452-460, 2007.
Shapira et al. "Role of Glycogen Synthase Kinase-3[Beta] in Early Depressive Behavior Induced by Mild Traumatic Brain Injury", Molecular and Cellular Neuroscience, 34: 571-577, 2007.
Ter Haar et al. "Structure of GSK3[Beta] Reveals a Primed Phosphorylation Mechanism", Nature Structural Biology, 8(7): 593-596, Jul. 2001.
Woodgett et al. "Multisite Phosphorylation of Glycogen Synthase. Molecular Basis for the Substrate Specificity of Glycogen Synthase Kinase-3 and Casein Kinase-II (Glycogen Synthase Kinase-5)", Biochimica et Biophysica Acta, 788: 339-347, 1984.
Communication Pursuant to Article 94(3) EPC Dated Feb. 7, 2017 From the European Patent Office Re. Application No. 14736462.4. (5 Pages).

* cited by examiner

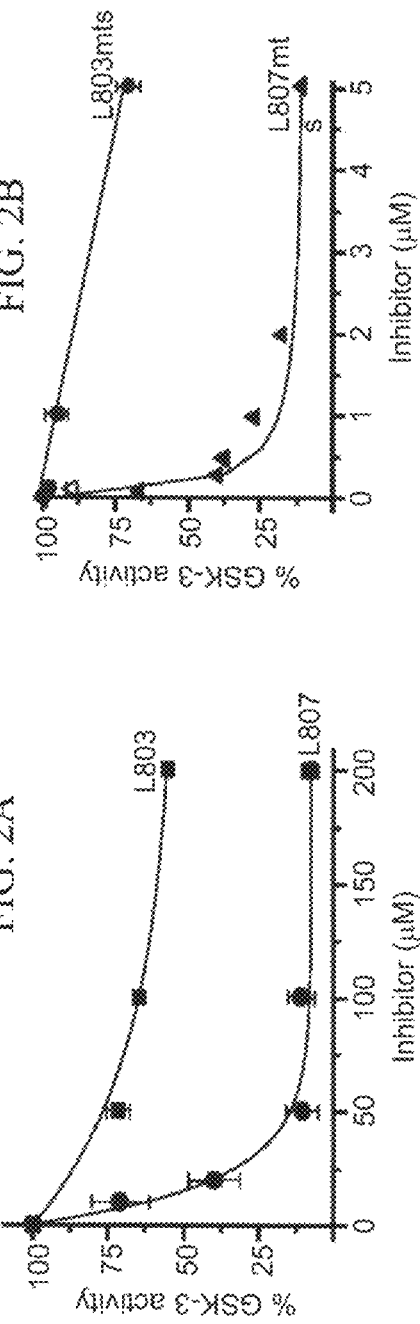
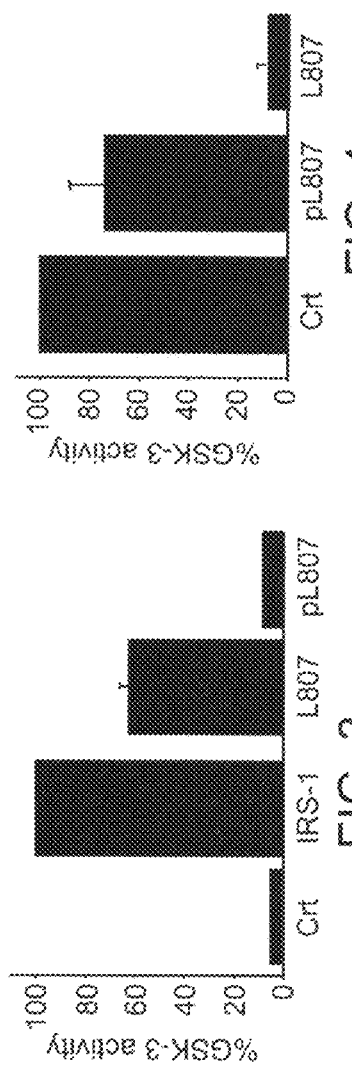
FIG. 2A
FIG. 2B
FIG. 3
FIG. 4

GLYCOGEN SYNTHASE KINASE-3 INHIBITORS

RELATED APPLICATIONS

This application is a National Phase of PCT Patent Application No. PCT/IL2014/050567 having International filing date of Jun. 24, 2014, which claims the benefit of priority under 35 USC §119(e) of U.S. Provisional Patent Application No. 61/838,347 filed on Jun. 24, 2013.

SEQUENCE LISTING STATEMENT

The ASCII file, entitled 6464OReplacementSL.txt, created on Sep. 4, 2016, comprising 22,179 bytes, which is incorporated herein by reference.

FIELD AND BACKGROUND OF THE INVENTION

The present invention, in some embodiments thereof, relates to novel glycogen synthase kinase-3 (GSK-3) inhibitors and, more particularly, but not exclusively, to novel selective inhibitors of glycogen synthase kinase-3 (GSK-3) and to the use of such inhibitors in, for example, the treatment of biological conditions associated with GSK-3 activity.

Protein kinases and phosphorylation cascades are essential for life and play key roles in the regulation of many cellular processes including cell proliferation, cell cycle progression, metabolic homeostasis, transcriptional activation and development. Aberrant regulation of protein phosphorylation underlies many human diseases, and this has prompted the development and design of protein kinase inhibitors. Most of the protein kinase inhibitors developed so far compete with ATP for its binding site. These inhibitors, although often very effective, generally show limited specificity due to the fact that the ATP binding site is highly conserved among protein kinases.

Other sites, such as the substrate's binding site, show more variability in their shape and amino acid compositions and may serve as favorable sites for drug design. Understanding of substrate recognition and specificity is thus essential for development of substrate competitive inhibitors. This knowledge, however, is limited by the scarce amount of structural data regarding substrate binding.

Glycogen synthase kinase-3 (GSK-3) is a constitutively active serine/threonine kinase that modulates diverse cellular functions including metabolism, cell survival and migration, neuronal signaling and embryonic development. Deregulation of GSK-3 activity has been implicated in the pathogenesis of human diseases such as, for example, type-2 diabetes, neurodegenerative disorders and psychiatric disorders. Selective inhibition of GSK-3 is thought to be of therapeutic value in treating these disorders [Bhat et al. (2004). *J. Neurochem.* 89, 1313-7; Cohen, P. & Goedert, M. (2004). *Nat. Rev. Drug Discov.* 3, 479-87; Meijer et al. (2004) *Trends Pharmacol Sci* 25, 471-80; Eldar-Finkelman et al. *Biochim Biophys Acta* 1804, 598-603; Martinez, A. & Perez, D. I. (2008) *J. Alzheimers Dis.* 15, 181-91].

Recently, it has been found that GSK-3 is also involved in the pathogenesis of cardiovascular diseases [Cheng et al. 2010 *J. Mol Cell Cardiol*, in press; Kerkela et al. 2008, *J. Clin. Invest.* 118:3609-18], of malaria and trypanosomiasis [Droucheau et al. 2004, *BBRC*, 1700:139-140; Ojo et al. 2008, *Antimicrob Agents Chemother*, 37107-3717], and in stem cell maintenance or differentiation [Wray et al. 2010 *Biochem Soc Trans* 1027-32].

In view of the wide implication of GSK-3 in various signaling pathways, development of specific inhibitors for GSK-3 is considered both promising and important regarding various therapeutic interventions as well as basic research.

Some mood stabilizers were found to inhibit GSK-3. However, while the inhibition of GSK-3 both by lithium chloride (LiCl) (WO 97/41854) and by purine inhibitors (WO 98/16528) has been reported, these inhibitors are not specific for GSK-3. In fact, it was shown that these drugs affect multiple signaling pathways, and inhibit other cellular targets, such as inositol monophosphatase (IMpase) and histone deacetylases.

Similarly, an engineered cAMP response element binding protein (CREB), a known substrate of GSK-3, has been described (Fiol et al, 1994), along with other potential GSK-3 peptide inhibitors (Fiol et al, 1990). However, these substrates also only minimally inhibit GSK-3 activity.

Other GSK-3 inhibitors have been reported. Two structurally related small molecules SB-216763 and SB-415286 (GlaxoSmithKline Pharmaceutical) that specifically inhibited GSK-3 were developed and were shown to modulate glycogen metabolism and gene transcription as well as to protect against neuronal death induced by reduction in PI3 kinase activity (Cross et al., 2001; Coghlan et al., 2000). Another study indicated that Induribin, the active ingredient of the traditional Chinese medicine for chronic myelocytic leukemia, is a GSK-3 inhibitor. However, Indirubin also inhibits cyclic-dependent protein kinase-2 (CDK-2) (Damiens et al., 2001). These GSK-3 inhibitors are ATP competitive and were identified by high throughput screening of chemical libraries. It is generally accepted that a major drawback of ATP-competitive inhibitors is their limited specificity (see, for example, Davies et al., 2000).

Some of the present inventors have previously reported of a novel class of substrate competitive inhibitors for GSK-3 [Plotkin et al. (2003) *J. Pharmacol. Exp. Ther.*, 974-980], designed based on the unique substrate-recognition motif of GSK-3 that includes a phosphorylated residue (usually serine) in the context of SXXXS(p) (where S is the target serine, S(p) is phosphorylate serine and X is any amino acid) [see also Woodgett & Cohen (1984) *Biochim. Biophys. Acta.* 788, 339-47; Fiol et al. (1987) *J. Biol. Chem.* 262, 14042-8]. Structural studies of GSK-3β identified a likely docking site for the phosphorylated residue; it is a positively charged binding pocket composed of Arg96, Arg180, and Lys205 [Dajani et al. (2001) *Cell* 105, 721-32; ter Haar et al. (2001) *Nature Structural Biology* 8, 593-6].

The short phosphorylated peptides patterned after the GSK-3 substrates behaved as substrate competitive inhibitors (Plotkin et al., 2003, supra), with the L803 peptide, KEAPPAPPQS(p)P (SEQ ID NO:4), derived from the substrate heat shock factor-1 (HSF-1) showing the best inhibition activity of those evaluated. An advanced version of L803, the cell permeable peptide L803-mts, was shown to promote beneficial biological activities in conditions associated with diabetes, neuron growth and survival, and mood behavior [Kaidanovich-Beilin & Eldar-Finkelman (2005) *J. Pharmacol. Exp. Ther.* 316:17-24; Rao et al. (2007) *Diabetologia* 50, 452-60; Kim et al. (2006) *Neuron* 52, 981-96; Chen et al. (2004) *Faseb J* 18, 1162-4; Kaidanovich-Beilin et al. (2004) *Biol. Psychiatry.* 55:781-4; Shapira et al. (2007) *Mol. Cell Neurosci.* 34, 571-7].

While further focusing on substrate recognition of GSK-3, three positions in the vicinity of the catalytic site (Phe67 in the P-loop, Gln89 and Asn95) were identified as important for GSK-3 substrates binding [Ilouz et al. (2006) *J. Biol. Chem.* 281, 30621-30], and a cavity bordered by loop 89-QDKRFKN-95 (SEQ ID NO:2) located in the vicinity of the GSK-3β catalytic core, has also been identified as a substrate binding subsite.

In-silico modeling of the interaction of GSK-3 with its substrates pCREB and p9CREB, corroborated by mutation experiments, suggested that the substrates bind in the deep trough between the N- and C-terminal lobes of the kinase, as illustrated in Background Art FIG. 1 (Ilouz et al. 2006, supra). It was further suggested that the pre-phosphorylated S133$_p$ residue is located in the phosphate binding pocket of GSK-3 formed by residues R96, R180 and K205, and the phosphorylation target S129 points toward they phosphate of ATP.

WO 2012/101599 describes further studies conducted for identifying sites of GSK-3 that play an important role in binding GSK-3 substrates. In these studies, a role of Phe93, as well as of other amino acids within the 89-95 loop of a GSK-3 enzyme, in interacting with GSK-3 substrates and hence with GSK-3 substrate competitive inhibitors, was uncovered, thereby indicating that a putative substrate competitive inhibitor should exhibit an interaction with the Phe93 residue, or with an equivalent amino acid thereof, in a GSK-3 enzyme Peptidic substrate competitive GSK-3 inhibitors were designed after the recognition motif of HSF while modifying the peptide's hydrophobic nature by replacing hydrophilic polar amino acids by hydrophobic amino acids residues such as alanine and proline. Exemplary such substrate competitive inhibitors, which feature a hydrophobic amino acid residue at the first position upstream the phosphorylated serine or threonine residue, exhibited improved activity compared to, for example, L803.

WO 2012/101601 describes additional studies in which initial models obtained by rigid body docking of selected L803 conformers to GSK-3β with the geometric-electrostatic-hydrophobic version of MolFit followed by filtering based on statistical propensity measures and solvation energy estimates, were subjected to molecular dynamics (MD) simulations. These computations provided further understanding on the binding of the inhibitor. The computational model structures, supported by experimental data, have shown that a modified L803 peptide, which features a Phe residue at the C-terminus of L803, and which is termed L803F, exhibits a substantially improved interaction with Phe 93, via its Pro8 and Phe12, and with the hydrophobic surface patch of GSK-3β.

Further in silico modeling suggested that while GSK-3 substrates interact with the positive pocket delimited by residues R96, R180 and K205, with the substrate binding cavity delimited by the P-loop and loop 89-95, with the protruding F93 residue, and with the hydrophobic surface patch opposite the P-loop, which consists of residues V214, Y216 and I217, the inhibitor L803 uses only part of the sub-sites mentioned above: the pre-phosphorylated serine binds in the positive pocket but the other contacts are hydrophobic (Licht-Murava et al., *J. Mol. Biol.* (2011) 408, 366-378). Thus, L803 interacts with GSK-3 F93 and with the hydrophobic patch but it does not interact with the P-loop or with the substrate binding cavity.

Additional background art includes U.S. Pat. Nos. 6,780, 625 and 7,378,432; WO 2004/052404 and WO 2005/000192; WO 01/49709; Liberman, Z. & Eldar-Finkelman, H. (2005) *J. Biol. Chem.* 280, 4422-8; Liberman et al. (2008) *Am. J. Physiol. Endocrinol. Metab.* 294, E1169-77; Bertrand et al. (2003) *J. Mol. Biol.* 333, 393-407; and Palomo et al. *J. Med. Chem.* (2012) Feb. 23; 55(4):1645-61.

SUMMARY OF THE INVENTION

According to an aspect of some embodiments of the present invention there is provided a peptide having the amino acid sequence II:

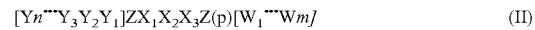

$$[Y_n\text{---}Y_3Y_2Y_1]ZX_1X_2X_3Z(p)[W_1\text{---}W_m] \qquad (II)$$

wherein:
n is 5, 6 or 7,
m is 1, 2, 3, 4 or 5;
m and n are such that the peptide consists of no more than 15 amino acid residues;
Z(p) is a phosphorylated serine residue or a phosphorylated threonine residue;
Z is a phosphorylatable serine residue or a phosphorylatable threonine residue;
$X_1$, $X_2$, $X_3$ and $W_1$-Wm is each independently any amino acid residue; and
$Y_1$-Yn comprises an amino acid sequence as set forth in SEQ ID NO:8:
Lys-Glu-$Y_3$-Pro-Pro (SEQ ID NO:8),
wherein $Y_3$ is any amino acid residue excepting a glutamic acid residue.

According to some of any of the embodiments of the present invention, $Y_3$ is an amino acid residue having a Log P higher than −3.

According to some of any of the embodiments of the present invention, $Y_3$ is selected from the group consisting of glycine residue, alanine residue, valine residue, leucine residue, isoleucine residue, proline residue, methionine residue, cysteine residue, tryptophan residue and phenylalanine residue.

According to some of any of the embodiments of the present invention, $Y_3$ is an alanine residue.

According to some of any of the embodiments of the present invention, at least one of n, m, $X_1$, $X_2$, $X_3$ and $W_1$-Wm is identical to a corresponding amino acid residue of HSF-1.

According to some of any of the embodiments of the present invention, Z is a serine residue.

According to an aspect of some embodiments of the present invention there is provided a peptide, being of no more than 15 amino acid residues, and having an amino acid sequence which comprises a $ZX_1X_2X_3Z(p)$ recognition motif of GSK-3, wherein Z(p) is a phosphorylated serine residue or a phosphorylated threonine residue; Z is a phosphorylatable serine residue or phosphorylatable threonine residue, and each of $X_1$, $X_2$ and $X_3$ is any amino acid,
the peptide exhibiting an inhibition activity towards GSK-3.

According to some embodiments of the present invention, the peptide is being such that when a GSK-3 reacts with a GSK-3 substrate in the presence of the peptide, an apparent Michaelis Constant (app Km value) of the GSK-3 substrate is higher than a Michaelis Constant (Km value) obtained in a similar assay in the absence of the peptide inhibitor.

According to some embodiments of the present invention, the peptide has an amino acid sequence upstream the Z residue in the recognition motif which is accountable for the inhibition activity.

According to some embodiments of the present invention, the amino acid sequence upstream the Z residue in the recognition motif comprises at least one amino acid residue which is such that when the Z is phosphorylated upon interaction with the catalytic binding site of GSK-3, a phosphorylated peptide obtained by this interaction exhibits a low dissociation constant (e.g., lower than 0.5 µM).

According to some embodiments of the present invention, the peptide is being such that the at least one amino acid residue upstream the phosphorylated serine residue or phosphorylated threonine residue in the phosphorylated peptide obtained by the interaction is in a proximity and orientation with respect to an amino acid residue within the catalytic binding site of GSK-3, which is accountable for the dissociation constant.

According to some embodiments of the present invention, the amino acid residue within the catalytic binding site is Phe93.

According to some embodiments of the present invention, the at least one amino acid residue upstream the phosphorylatable serine or threonine residue is selected from the group consisting of a non-polar amino acid residue, a non-charged amino acid residue (at a physiological pH) and a hydrophobic amino acid residue.

According to some embodiments of the present invention, the amino acid residue upstream the Z is any amino acid residue excepting glutamic acid, glutamine, aspartic acid, aspargine, lysine, and histidine.

According to some embodiments of the present invention, the amino acid upstream the Z is selected from the group consisting of alanine, glycine, valine, leucine, isoleucine, proline residue, methionine residue, cysteine residue, tryptophan residue, tyrosine residue and phenylalanine.

According to some embodiments of the present invention, the peptide has an amino acid sequence I:

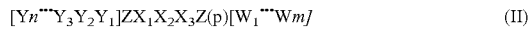

$$[Y_n\text{---}Y_3Y_2Y_1]ZX_1X_2X_3Z(p)[W_1\text{---}W_m]$$ (II)

wherein, m equals 1, 2, 3, 4 or 5;

n is 3, 4, 5, 6 or 7, such that m and n are such that the peptide consists of no more than 15 amino acid residues;

Z(p) is the phosphorylated serine residue or the phosphorylated threonine residue;

Z is the phosphorylatable serine residue or the phosphorylatable threonine residue;

$X_1$, $X_2$, $X_3$, $Y_1$-Yn and $W_1$-Wm are each independently an amino acid residue of the substrate, wherein at least one of the $Y_1$-Yn is the amino acid residue upstream the phosphorylatable serine or threonine residue, as described in any one of the embodiments herein.

According to some embodiments of the present invention, m equals 1 or 2.

According to some embodiments of the present invention, n and m are such that the peptide consists of 10 to 13 amino acid residues.

According to some embodiments of the present invention, $Y_3$ is the amino acid residue upstream the phosphorylatable serine or threonine residue, as described in any one of the respective embodiments.

According to some embodiments of the present invention, $Y_3$ is selected from the group consisting of glycine residue, alanine residue, valine residue, leucine residue, isoleucine residue, proline residue, methionine residue, cysteine residue, tryptophan residue, tyrosine residue, and phenylalanine residue.

According to some of any of the embodiments of the present invention, Z(p) is a phosphorylated serine residue.

According to some of any of the embodiments of the present invention, m equals 1.

According to some of any of the embodiments of the present invention, $W_1$ is a proline residue.

According to some of any of the embodiments of the present invention, m equals 1 and $W_1$ is a hydrophobic amino acid residue.

According to some of any of the embodiments of the present invention, $W_1$ is a phenylalanine residue.

According to some of any of the embodiments of the present invention, one or more of $X_1$, $X_2$ and $X_3$ is a hydrophobic amino acid residue.

According to some of any of the embodiments of the present invention, the one or more hydrophobic amino acid residue is independently selected from the group consisting of a proline residue and an alanine residue.

According to some of any of the embodiments of the present invention, $X_1$ is a proline residue.

According to some of any of the embodiments of the present invention, $X_1$ and $X_2$ are each a proline residue.

According to some of any of the embodiments of the present invention, n is 5.

According to some of any of the embodiments of the present invention, $Y_1$-$Y_5$ has the amino acid sequence as set forth in SEQ ID NO:8.

According to some of any of the embodiments of the present invention, the $Y_1$-$Y_5$ has an amino acid sequence Lys-Glu-Ala-Pro-Pro, as set forth in having SEQ ID NO:37.

According to some embodiments of the invention, the peptide has an amino acid sequence as set forth in SEQ ID NO:9.

According to some of any of the embodiments of the present invention the peptide is further comprising a hydrophobic moiety attached thereto.

According to some embodiments of the invention, the hydrophobic moiety is attached to the N-terminus of the peptide.

According to some embodiments of the invention, the hydrophobic moiety is selected from the group consisting of a fatty acid and a fatty acid attached to an amino acid residue.

According to some embodiments of the invention, the fatty acid is myristic acid.

According to some embodiments of the invention, the peptide has the amino acid sequence as set forth in SEQ ID NO:10.

According to an aspect of some embodiments of the present invention there is provided a pharmaceutical composition comprising, as an active ingredient, the peptide as described herein, in any one of the respective embodiments, and a pharmaceutically acceptable carrier.

According to some embodiments of the invention, the pharmaceutical composition is packaged in a packaging material and identified in print, on or in the packaging material, for use in inhibiting an activity of GSK-3.

According to some embodiments of the invention, the pharmaceutical composition is packaged in a packaging material and identified in print, on or in the packaging material, for use in the treatment of a biological condition associated with GSK-3 activity.

According to an aspect of some embodiments of the present invention there is provided a peptide as described herein, for use in inhibiting an activity of GSK-3.

According to an aspect of some embodiments of the present invention there is provided a peptide as described herein for use in the treatment of a biological condition associated with GSK-3 activity.

According to an aspect of some embodiments of the present invention there is provided a method of inhibiting an activity of GSK-3, the method comprising contacting cells expressing GSK-3 with an effective amount of the peptide as described herein.

According to an aspect of some embodiments of the present invention there is provided a use of the peptide as described herein in the manufacture of a medicament for inhibiting an activity of GSK-3 activity.

According to some embodiments of the invention, the activity is a phosphorylation activity and/or an autophosphorylation activity.

According to an aspect of some embodiments of the present invention there is provided a method of treating a biological condition associated with GSK-3 activity, the method comprising administering to a subject in need thereof a therapeutically effective amount of the peptide as described herein.

According to an aspect of some embodiments of the present invention there is provided a use of the peptide as described herein in the manufacture of a medicament for treating a biological condition associated with GSK-3 activity.

According to some of any of the respective embodiments of the invention, the biological condition is associated with overexpression of GSK-3.

According to some of any of the respective embodiments of the invention, the biological condition is selected from the group consisting of obesity, non-insulin dependent diabetes mellitus, an insulin-dependent condition, an affective disorder, major depression, a neurodegenerative disease or disorder, a psychotic disease or disorder, a cardiovascular disease or disorder, a condition associated with a pathogenic parasite, and a condition treatable by stem cell transplantation and/or stem cells maintenance.

According to an aspect of some embodiments of the present invention there is provided a method of computationally screening for a putative substrate-competitive peptide inhibitor of GSK-3, substantially as described herein.

According to an aspect of some embodiments of the present invention there is provided a peptide having the amino acid sequence II*:

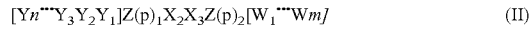

wherein:

n, m, $X_1$, $X_2$, $X_3$, $W_1$-Wm and $Y_1$-Yn are as described herein for any of the embodiments of amino acid sequences I and II, and any combination thereof; and $Z(p)_1$ and $Z(p)_2$ are each independently a phosphorylated serine residue or a phosphorylated threonine residue.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
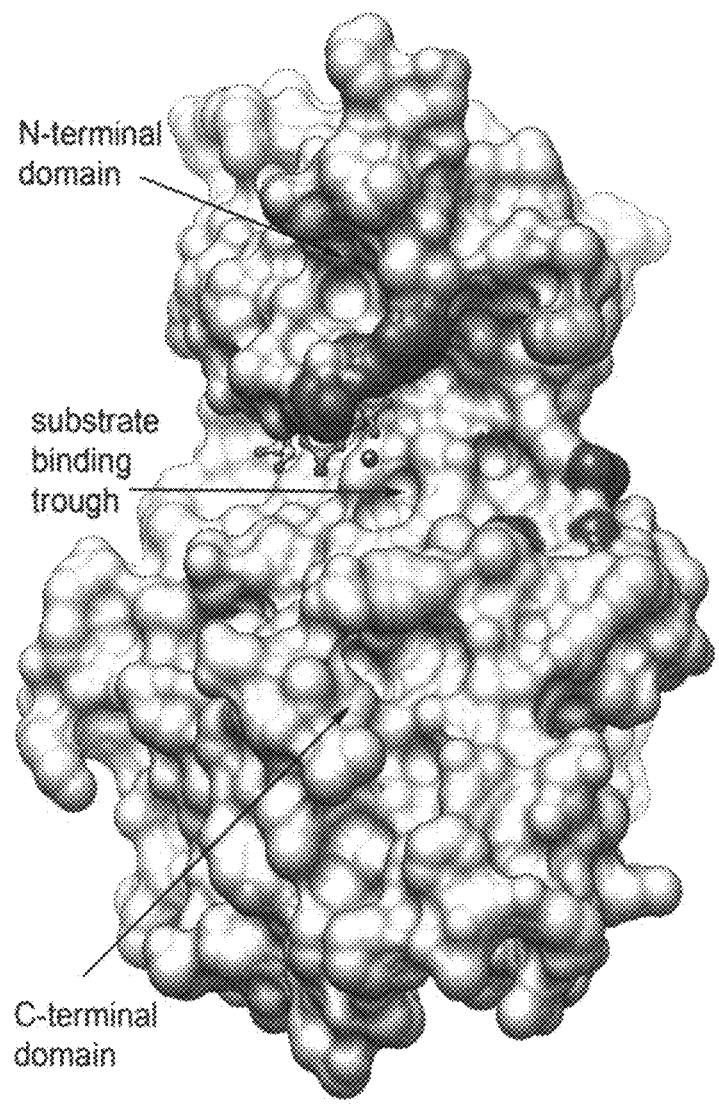

FIG. 1 (Background Art) presents an image of computational modeling results showing sub-sites within the substrate binding trough of GSK-3, in which the solvent accessible surface of GSK-3 is shown in gray, the P-loop indicated in dark green, Q89 and N95 within the substrate binding cavity in orange, F93 in light green, the positive ends of the side chains of R96, R180 and K205, delimiting the phosphate binding pocket, in blue, the hydrophobic patch residues V214, Y216 and I217 in beige (residue numbering as in GSK-3 isoform β), and ATP-$Mg^{2+}$ carbon, nitrogen, oxygen, phosphor and Mg are colored in gray, blue, red, orange and dark gray, respectively.

Figure 5:
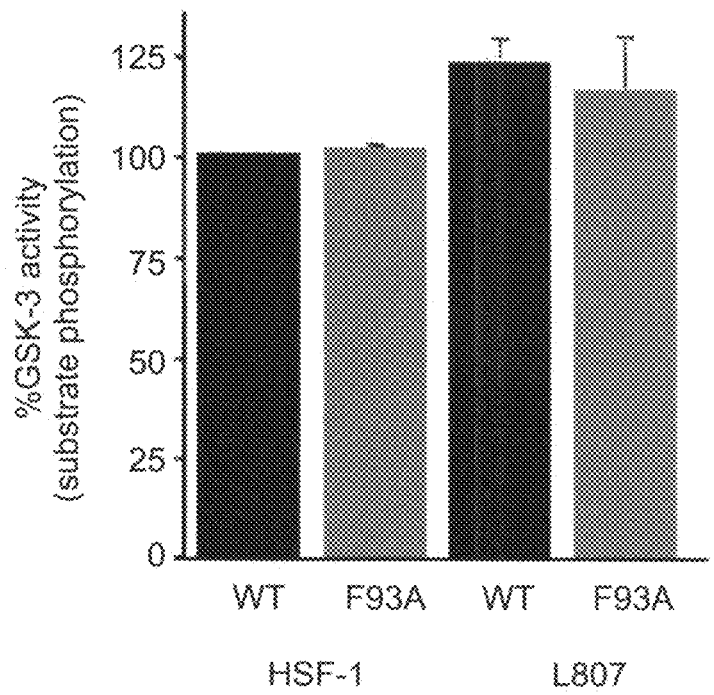
Figure 6:
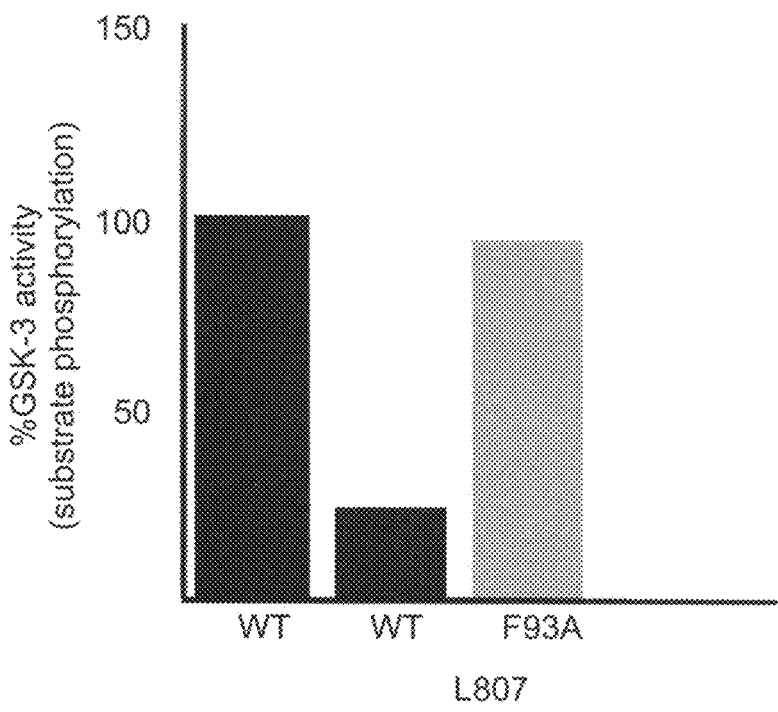
Figure 7:
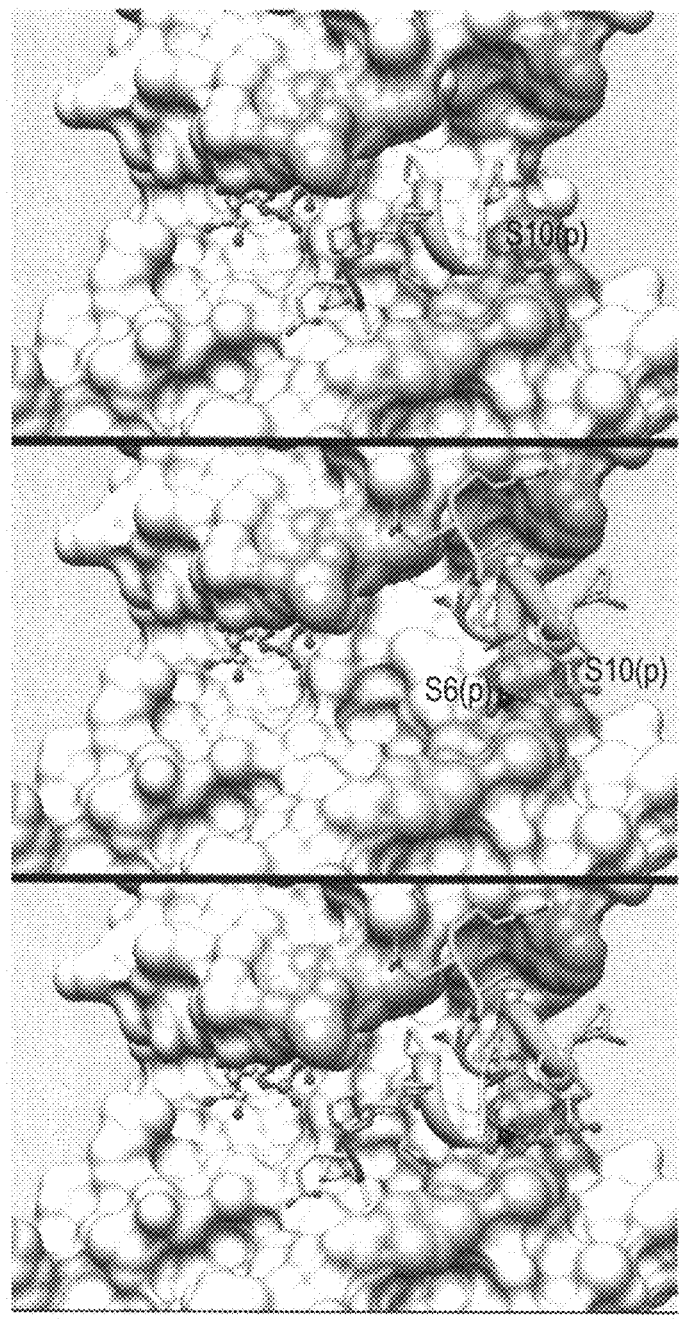
Figures 8A, 8B:
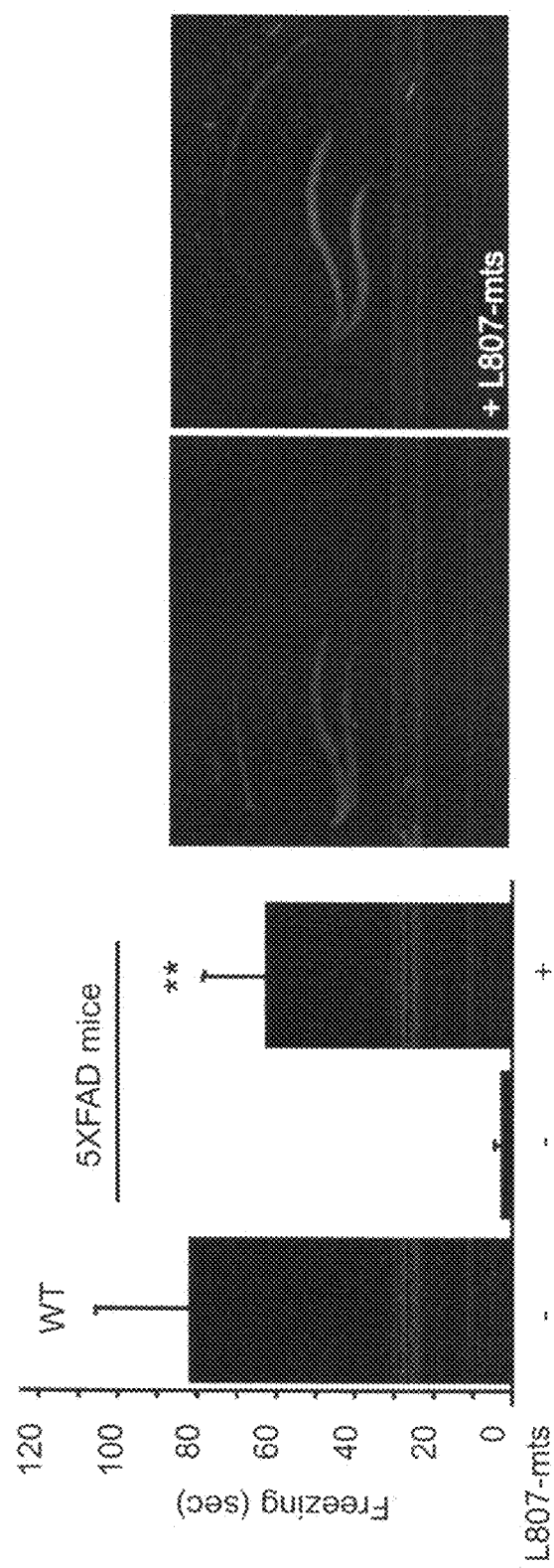

FIGS. 2A-B present dose-response comparative plots showing the substrate-competitive inhibition of GSK-3β activity by L807 (FIG. 2A) and L807-mts (FIG. 2B), as exemplary GSK-3 inhibitors according to some embodiments of the present invention, compared to L803 and L803-mts, using pIRS-1 as a substrate (Substrate phosphorylation obtained in reaction with no inhibitor was defined as 100%, and results presented are means of two independent experiments each performed in duplicate±SEM);

FIG. 3 is a bar graph showing peptide phosphorylation by GSK-3β as determined in in vitro kinase assays performed with pIRS-1, L807, or pL807 as substrates, using $^{32}$P-γ-ATP (results presented are means of two independent experiments each performed in duplicate±SEM);

FIG. 4 is a bar graph showing the inhibition of GSK-3β activity by L807 and pL807-mts, as determined in in vitro kinase assays performed with pIRS-1 as a substrate (Substrate phosphorylation obtained in reaction with no inhibitor was defined as 100%, and results presented are means of two independent experiments each performed in duplicate±SEM);

FIG. 5 is a bar graph showing peptide phosphorylation by WT GSK-3β and its F93A mutant, as determined in in vitro kinase assays performed with HSF-1 or L807 as substrates, using $^{32}$P-γ-ATP (Substrate phosphorylation using HSF-1 as substrate defined as 100%) and results presented are means of two independent experiments each performed in duplicate±SEM);

FIG. 6 is a bar graph showing the inhibition of phosphorylation activity of WT GSK-3β and of its F93A mutant by L807, as determined in in vitro kinase assays performed with pIRS-1 as a substrate (Substrate phosphorylation obtained in reaction with no inhibitor was defined as 100%, and results presented are means of two independent experiments each performed in duplicate±SEM);

FIG. 7 presents images of computational docking of L807 (top panel), pL807 (central panel) and of both L807 and pL807 (bottom panel), predicting the binding mode of the peptides to GSK-3, with the solvent accessible surface of GSK-3 shown in gray, the positive cavity in blue, the P-loop in green, the substrate binding pocket and F93 (Q89, F93 and N95) in orange and the hydrophobic surface (V214, Y216 and I217) in beige; and FIGS. 8A-B present a bar graph (FIG. 8A) showing the freezing time duration determined in WT mice (left bar), non-treated 5XFAD mice (middle bar) and L807-mts-treated 5XFAD mice (right bar), as evaluated in the contextual fear-conditioning test (analyses are means of 5 or 6 animals±SEM; **p<0.005), and representative histological images (FIG. 8B) of PFA-fixed hemi-brain sections obtained from L807-mts-treated (right image) or non-treated (left image) 5XFAD mice, upon staining with Congo red/Dapi.

DESCRIPTION OF SPECIFIC EMBODIMENTS OF THE INVENTION

The present invention, in some embodiments thereof, relates to novel glycogen synthase kinase-3 (GSK-3) inhibitors and, more particularly, but not exclusively, to novel selective inhibitors of glycogen synthase kinase-3 (GSK-3) and to the use of such inhibitors in, for example, the treatment of biological conditions associated with GSK-3 activity.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Some of the present inventors have previously described that peptides designed after the recognition motif of a GSK-3 substrate are useful as GSK-3 substrate competitive inhibitors. See, for example, WO 01/49709 and U.S. Patent Application No. 20020147146, which are incorporated by reference as if fully set forth herein.

These peptides were designed further to the findings that GSK-3 has a unique recognition motif, and thus that short peptides which are designed with reference to this motif are highly specific GSK-3 inhibitors.

The unique recognition motif of GSK-3, as set forth in SEQ ID NO:1, is $ZX_1X_2X_3Z(p)$, where Z is serine or threonine, each of $X_1$, $X_2$ and $X_3$ is any amino acid, and $Z(p)$ is phosphorylated serine or phosphorylated threonine.

The previously disclosed peptides were designed based on this recognition motif, and upon determining in various assays the features which should render a peptide an efficient GSK-3 inhibitor. In these assays it was found, for example, that the phosphorylated serine or threonine residue in the motif is necessary for binding. Without this residue, the peptide will neither be a substrate nor an inhibitor. It was further determined that a serine (or threonine) residue upstream of the phosphorylated serine (or threonine) residue separated by three additional residues renders the peptide a GSK-3 substrate, whereas replacement of this serine or threonine residue by any other amino acid, preferably alanine, converts the substrate to a GSK-3 inhibitor. It was further found that the number of the additional residues, outside the recognition motif, affects the inhibition potency of the peptide, such that, for example, a total number of between 7 and 50, preferably, between 7 and 20, or between 7 and 15, and more preferably between 10 and 13 amino acid residues, is preferable.

Hence, it was previously described that peptides having the general amino acid sequence denoted herein as general sequence I*:

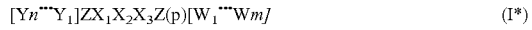
$$[Yn\text{...}Y_1]ZX_1X_2X_3Z(p)[W_1\text{...}Wm] \quad (I^*)$$

wherein m and n are such that the total number of amino acid residues in as defined hereinabove; Z(p) is a phosphorylated serine residue or a phosphorylated threonine residue; Z is any amino acid residue excepting serine residue or threonine residue; and $X_1$, $X_2$, $X_3$, $Y_1$-Yn and $W_1$-Wm are each independently any amino acid residue, are highly efficient, specific inhibitors of GSK-3. See, for example, U.S. Pat. Nos. 6,780,625 and 7,378,432; WO 2004/052404 and WO 2005/000192; and WO 01/49709, which are incorporated by reference as if fully set forth herein.

It is noted that since these previously described GSK-3 inhibitors were designed so as to modify an amino acid sequence of known GSK-3 substrates, the nature of the amino acid residues presented by variables $X_1$, $X_2$, $X_3$, $Y_1$-Yn and $W_1$-Wm in the amino acid sequence I* was typically defined per the corresponding residues in the known GSK-3 substrate, namely, $X_1$, $X_2$, $X_3$ were the same as corresponding amino acid residues between a serine and a phosphorylated serine in a known GSK-3 substrate, $Y_1$-Yn were the same as the amino acid residues upstream the serine residue, and $W_1$-Wm were the same as the amino acid residues downstream the phosphorylated serine (or threonine) residue, of a known GSK-3 substrate.

It was further described that preferred peptides are those having an alanine residue at the Z position, having any amino acid residue excepting glutamic acid as $Y_3$, and/or having between 7 and 20 amino acid residues, preferably between 10 and 13 amino acid residues and more preferably between 10 and 11 amino acid residues.

It was further described that a conjugate of the peptide inhibitor described above and a hydrophobic moiety, such as a fatty acid, attached, directly or indirectly, at the N-terminus of the polypeptide, exerts higher inhibition of GSK-3 activity (see, for example, WO 2004/052404).

These peptides were defined as substrate-competitive inhibitors of GSK-3.

As is well known in the art, substrate competitive enzyme inhibitors act by binding to the catalytic domain of an enzyme, thus reducing the proportion of enzyme molecules that are bound to the enzyme during the catalytic process.

While recognizing that the development of substrate competitive inhibitors depends on a molecular understanding of substrate recognition of protein kinases, efforts have been made in order to define the catalytic binding site of GSK-3. Thus, Phe67, Gln89 and Asn95 within the catalytic binding site of GSK-3β have been reported to play a role in substrates' binding [see, Ilouz et al., 2006, supra), and a cavity bordered by loop 89-QDKRFKN-95 (as set forth in SEQ ID NO:2), located in the vicinity of the GSK-3β catalytic core, has been identified as a promiscuous substrate binding subsite.

The role of the 89-95 loop in GSK-3β substrate binding has been further explored and it was identified that in addition to Gln89 and Asn95 in this loop, Phe93 is also important for substrate binding. Based on these understandings, additional substrate-competitive peptide inhibitors of GSK-3 were designed, following the general sequence I* as described hereinabove, while better defining preferred amino acids residues at positions $X_3$ and $W_1$. See, for example, WO 2012/101599 and WO 2012/101601.

In a search for improved GSK-3 inhibitors, the present inventors have further explored the effect of individual replacements of amino acid residues within the amino acid sequence of known GSK-3 substrates and inhibitors. As demonstrated in the Examples section that follows, it was surprisingly uncovered that a peptide which has an amino acid sequence derived from a known GSK-3 substrate, such as HSF-1, in which only the Glu residue at the third position upstream the serine residue within the $ZX_1X_2X_3Z(p)$ recognition motif is replaced by a non-polar residue such as alanine, while the serine residue is maintained, acts as a highly potent inhibitor of GSK-3.

Exemplary such inhibitors are termed herein L807 (SEQ ID NO:9) and L807-mts (SEQ ID NO:10).

As further described in the Examples section that follows, activity assays and computational docking led to the assumption that once such a peptide is phosphorylated, the doubly phosphorylated peptide (for example, pL807; SEQ ID NO:9) remains bound in the catalytic groove of GSK-3, possibly upon conformational changes, and does not dissociate easily. Without being bound by any particular theory, it is assumed that the lack of dissociation is a result of the replacement of the Glu residue.

In efforts to establish the above assumption, the binding mode of the substrate HSF-1 (SEQ ID NO:3; KEEPPSPPQS (p)P; also denoted herein as pHSF-1), where S(p) denotes phosphorylated serine) was studied and compared to the binding mode of the inhibitor L803 (KEAPPAPPQS(p)P; SEQ ID NO:4), which differs from pHSF-1 in two positions (an alanine residue instead of serine residue at the fourth position upstream the phosphorylated serine residue, and an alanine residue instead of glutamic acid residue as the third amino acid residue upstream the serine residue), and with L807 (SEQ ID NO:9) which differs from pHSF-1 in only one position (the third amino acid residue upstream the serine residue). Computational and molecular tools were used in these studies and have uncovered that the modification made in L807 indeed changed both the peptide's conformation and its binding mode, after its phosphorylation, possibly favoring binding to the hydrophobic sub-sites within the GSK-3 substrate binding trough.

For example, it has been demonstrated that L807 is phosphorylated by a GSK-3 F93A mutant, hence acts as a substrate of such a mutant, yet it does not act as an inhibitor of the F93A mutant. It has further been demonstrated that pL807, but not L807 and pHSF-1, is arranged within the catalytic binding site of GSK-3 in close proximity and orientation to Phe93 of GSK-3β, thus corroborating with the experimental data obtained with the F93A mutant.

Without being bound by any particular theory, it is suggested that due to its stronger interactions with Phe93, the dissociation constant of the pL807 variant generated upon the binding of L807 to GSK-3, is much lower than the dissociation constant of the corresponding phosphorylated HSF-1 variant generated upon the binding of pHSF-1 to GSK-3, and thus renders it an efficient inhibitor of GSK-3.

The fact that the newly designed peptides act both as substrates and inhibitors of GSK-3 is highly advantageous since their inhibition capacity is dependent upon GSK-3 activity (as the peptide needs to be phosphorylated first by GSK-3 in order to become an inhibitor). Hence, the level of the doubly phosphorylated peptide, which is the actual inhibitor species that is produced within the GSK-3 catalytic cavity, is directly related to GSK-3 activity. This pathway renders these newly designed peptide highly potent candidates for treating pathological conditions associated with increased GSK-3 activity, by being disease-selective inhibitors and thus highly safe for clinical use.

As used herein throughout, "GSK-3 enzyme", which is also referred to herein simply as GSK-3, describes a polypeptide having an amino acid sequence of a known GSK-3 family member (e.g., GSK-3α or GSK-3β). Unless otherwise indicated, this term refers to a wild-type GSK-3 enzyme. A GSK-3 enzyme is identified by the EC number EC 2.7.11.26. While the amino acid of GSK-3 is highly conserved, a wild-type GSK-3 can be GSK-3 of a mammal (e.g., human) or of any other organism, including microorganisms. An amino acid sequence of an exemplary GSK-3, human GSK-3β, is set forth in SEQ ID NO:5. A GSK-3 enzyme as used herein is homologous to SEQ ID NO:5 by at least 50%, at least 60%, at least 70%, at least 80%, at least 90% or can be 100% homologous.

By "wild-type" it is meant that the typical form of the enzyme as it occurs in nature, e.g., in an organism. A wild-type GSK-3 enzyme encompasses an enzyme isolated from an organism, a chemically synthesized enzyme and a recombinantly prepared enzyme.

Herein throughout, "a mutant of GSK-3 (or of GSK-3β)" is also referred to herein as "mutated GSK-3 enzyme" and is used to describe a polypeptide which differs from a corresponding wild-type GSK-3 (i.e., the starting point GSK-3) by at least one mutation (e.g., substitution).

A wild-type GSK-3 is as defined hereinabove for GSK-3.

A F93 mutant of GSK-3 is used herein to describe a mutated GSK-3 enzyme in which the amino acid substitution (mutation) is at position 93 of the 89-95 subunit. In most of the living organisms expressing GSK-3, this position corresponds to F93 (Phe93), as is in e.g., human GSK-3β.

A F93A mutant of GSK-3 (which is also referred to herein as F93) is used herein to describe a mutated GSK-3 enzyme in which Phe residue at position 93 of the enzyme is substituted by Alanine (Ala or A).

The amino acid sequence of an exemplary F93A mutant of GSK-3 is as set of forth in SEQ ID NO:6. The GSK-3 mutant as used herein is homologous to SEQ ID NO:6 by at least 50%, at least 60%, at least 70%, at least 80%, at least 90% or can be 100% homologous, as long as the substitution at position 93 is maintained.

Recombinant techniques, as described herein, are preferably used to generate the GSK-3 mutant. Alternatively, the mutant can be prepared by chemical synthesis, using, for example, solid phase synthesis as described herein.

Herein throughout, whenever a three-letter abbreviation of an amino acid is followed by a number it is meant the number of the indicated amino acid residue along the amino acid sequence downstream the N-terminus of the enzyme. The three-letter abbreviations described herein are as commonly used in the art.

By "position" it is meant a coordinate of the amino acid, whereby the indicated coordinate encompasses also an equivalent amino acid, as defined herein.

As used herein, an equivalent amino acid refers to an amino acid which is homologous (i.e., corresponding in position in either primary or tertiary structure) and/or analogous to a specific residue or portion thereof in a given sequence of GSK-3 or of a GSK-3 substrate (or inhibitor).

As used herein, the phrase "catalytic domain" describes a region of an enzyme, a GSK-3, in which the catalytic reaction occurs. This phrase therefore describes this part of an enzyme in which the substrate and/or other components that participate in the catalytic reaction interacts with the enzyme. In the context of the present embodiments, this phrase is particularly used to describe this part of an enzyme (a GSK-3) to which the substrate binds during the catalytic activity (e.g., phosphorylation). This phrase is therefore also referred to herein and in the art, interchangeably, as "substrate binding pocket", "catalytic site" "active site" and the like.

As used herein, the phrases "binding site", "catalytic binding site" or "binding subsite", which are used herein interchangeably, describe a specific site in the catalytic domain that includes one or more reactive groups through which the interactions of the enzyme with the substrate and/or an inhibitor can be effected. Typically, the binding site is composed of one or two amino acid residues, whereby the interactions typically involve reactive groups at the side chains of these amino acids.

As is well known in the art, when an enzyme interacts with a substrate or an inhibitor, the initial interaction rapidly induces conformational changes in the enzyme and/or substrate and/or inhibitor that strengthen binding and bring enzyme's binding sites close to functional groups in the substrate or inhibitor. Enzyme-substrate/inhibitor interactions orient reactive groups present in both the enzyme and the substrate/inhibitor and bring them into proximity with one another. The binding of the substrate/inhibitor to the enzyme aligns the reactive groups so that the relevant molecular orbitals overlap.

Thus, an inhibitor of an enzyme is typically associated with the catalytic domain of the enzyme such that the reactive groups of the inhibitor are positioned in sufficient proximity to corresponding reactive groups (typically side chains of amino acid residues) in the enzyme catalytic binding site, so as to allow the presence of an effective concentration of the inhibitor in the catalytic binding site and, in addition, the reactive groups of the inhibitor are positioned in a proper orientation, to allow overlap and thus a strong chemical interaction and low dissociation. An inhibitor therefore typically includes structural elements that are known to be involved in the interactions, and may also have a restriction of its conformational flexibility, so as to avoid conformational changes that would affect or weaken its association with catalytic binding site.

As discussed hereinabove, the present inventors have designed novel peptides, which are based on the recognition motif of a GSK-3 substrate, and are further designed to feature defined characteristics which provide for increased interaction of the peptide with the catalytic binding site of GSK-3, and particularly with an amino acid at position 93 of the enzyme, preferably with Phe93 (or an equivalent amino acid residue, as defined herein).

Thus, newly designed peptide inhibitors of GSK-3 are disclosed herein.

According to an aspect of some embodiments of the present invention there is provided a peptide having an amino acid sequence which comprises a $ZX_1X_2X_3Z(p)$ recognition motif of GSK-3, wherein $Z(p)$ is a phosphorylated serine residue or a phosphorylated threonine residue; Z is a serine residue or threonine residue; and each of $X_1X_2X_3$ is independently any amino acid residue.

In some embodiments, the peptide is being of no more than 20 amino acid residues, or no more than 15 amino acid residues in length. In some embodiments, the peptide is 10-13 amino acids residues in length.

As known in the art, in GSK-3 substrates, which comprise the $ZX_1X_2X_3Z(p)$ recognition motif as defined herein and as set forth in SEQ ID NO:1, the serine or threonine residue denoted as Z in the recognition motif is phosphorylated by an ATP molecule within the catalytic domain of the enzyme, when it contacts GSK-3. Such serine or threonine residues within the recognition motif can therefore be referred to as "phosphorylatable" residues or, interchangeably, as "GSK-3-phosphorylatable" residues or "GSK-3 phosphorylation target" residues, and are phosphorylated by GSK-3 when contacting the catalytic domain of GSK-3.

Since a peptide as described herein comprises the recognition motif of GSK-3, when it contacts GSK-3, it interacts with GSK-3 catalytic domain and the phosphorylatable serine or threonine residue Z is phosphorylated, to thereby generate a phosphorylated peptide.

Such a phosphorylated peptide comprises an amino acid sequence identical to that of the peptide as described herein, except that it comprises the amino acid sequence $Z(p)$ $X_1X_2X_3Z(p)$ (SEQ ID NO:7) instead of the recognition motif sequence as set forth in SEQ ID NO:1.

However, a peptide as described herein differs from other substrates of GSK-3, which often comprise the $ZX_1X_2X_3Z$ (p) recognition motif, by being capable of exhibiting an inhibition activity towards GSK-3.

Exemplary peptides according to some embodiments of the present invention are capable of exhibiting an inhibitory activity of GSK-3 by reducing the enzyme's activity by at least 20%, at least 30%, at least 40%, at least 50%, at least 60%, at least 70%, at least 80%, at least 90%, and even by higher values, at a peptide concentration as described in the Examples section that follows.

In some embodiments, the inhibition activity of the peptide as described herein is a competitive inhibition, as this term is known in the art.

In some embodiments, the peptide is capable of increasing the apparent Km value (Km app) of a GSK-3 substrate, when the phosphorylation activity of GSK-3 is measured in the presence of the GSK-3 substrate and the peptide, compared to the Km value measured for the phosphorylation activity of GSK-3 in the presence of the GSK-3 substrate only (in the absence of a peptide as described herein).

It is noted herein that when two substrates of an enzyme are reacted together with an enzyme, the Km value of the enzyme/substrate catalysis for each of the substrates remains unchanged.

However, when a peptide as described herein, and another GSK-3 substrate are reacted with GSK-3, the apparent Km of the other GSK-3 substrate is increased, and such an increase in indicative of the inhibitory activity of the peptide towards GSK-3.

As is well known in the art, Km (Michaelis Constant), is represented by the following equation:

$Km=[E][S]/[ES]$, and is measured by measuring the initial reaction rate according to the following equation:

$V=V\max[S]/Km+[S]$.

When a competitive inhibitor is present in an enzyme/substrate mixture, apparent Km is defined as:

$Km(app)=Km(1+[I]/K_i)$, with $K_i$ being the inhibitor's dissociation constant and [I] is the inhibitor concentration, and is measured by measuring the reaction rate according to the following equation:

$V=V\max[S]/Km(app)+[S]$.

Thus, in the case of the peptide as described herein (which is assumed to be a substrate-competitive inhibitor), at low substrate concentrations, reaction rate of the enzyme/substrate reaction is lower and apparent Km is higher.

Measuring Km and apparent Km of a substrate can be performed by methods well-known in the art. An exemplary method is described in the Examples section that follows.

It is noted that as is known in the art, Km values can be determined using the double-reciprocal Lineweaver-Burk equation and corresponding graphs, in which the γ-intercept is 1/Vmax; the x-intercept is −1/KM; and the slope is KM/Vmax. In Lineweaver-Burk graphs for competitive inhibitors, increase in Km value is shown, whereby Vmax stays the same. On double reciprocal plot, competitive inhibitor swifts the x-axis (1/[S]) to the right towards zero compared to the slope with no inhibitor present.

In some embodiments, the peptide as described herein comprises at least one amino acid residue upstream the phosphorylatable serine or phosphorylatable threonine residue (Z) in the recognition motif sequence within the peptide, which is such that when the phosphorylatable serine or threonine residue is phosphorylated upon contacting the catalytic domain of GSK-3, a phosphorylated peptide which is obtained by this contacting features a phosphorylated peptide-enzyme complex which exhibits a low dissociation constant.

As is known in the art, the term "upstream" with respect to an amino acid residue within a peptide, describes another amino acid within the peptide that is positioned between the indicated amino acid residue and the N-terminus of the peptide. Similarly, the term "downstream" with respect to an amino acid residue within a peptide, describes another amino acid within the peptide that is positioned between the indicated amino acid residue and the C-terminus of the peptide. These acceptable definitions are in line with the amino acid sequences of peptides which are read from the N-terminus to the C-terminus.

In some embodiments, the phosphorylated peptide-enzyme complex exhibits a dissociation constant which is lower than 2 μM, or lower than 1 μM, or lower than 0.5 μM, or lower than 0.1 μM, or even lower, with any value lower than 2 μM being contemplated.

As used herein and in the art, a "dissociation constant" represents an affinity between two entities according to the following equation:

$$Kd=[E][P^*]/[A-P^*]$$

wherein [E] is the concentration of an enzyme (herein GSK-3); [P*] is the concentration of the phosphorylated peptide as described herein, and can be assumed to be equivalent to the concentration of the peptide as described herein (prior to contacting GSK-3); and [A-P*] represents the phosphorylated peptide-complex as described herein.

Determining a dissociation constant of the phosphorylated peptide can be performed using methods known in the art.

It is to be noted that in native substrates of enzymes, the value Kd, when determined for the product obtained in an enzymatic reaction, is higher than 1 μM and is typically higher than 2, 3, 4, 5, 10, 20, 30 and even higher than 100 μM, since once such a product is obtained, it dissociates from the enzyme so as to render the enzyme's catalytic binding site free for further interactions with other substrate's molecules.

The low Kd of the phosphorylated peptide described herein therefore renders it a substrate-competitive inhibitor of the enzyme.

According to some embodiments of the present invention, a peptide as described herein is such that features strong association with the catalytic binding site of GSK-3 upon being phosphorylated at the catalytic domain of the enzyme, whereby the one or more amino acid residue(s) upstream the phosphorylatable serine or threonine residue (Z) is accountable for this strong association.

In some embodiments, the peptide is such that, upon contacting the GSK-3 catalytic binding site, the phosphorylatable serine or threonine residue (Z) is phosphorylated, and the one or more amino acid residue(s) upstream the now-phosphorylated serine or threonine residue in the phosphorylated peptide obtained by such contacting is in a proximity and orientation, as defined hereinabove, with respect to an amino acid residue within the catalytic binding site of GSK-3, and these proximity and orientation are accountable to said dissociation constant.

According to some embodiments of the present invention, the amino acid residue within the catalytic binding site (to which the amino acid residue upstream the phosphorylatable serine or threonine is in proximity and orientation that accounts for the strong association) is Phe93.

Thus, in some embodiments, the amino acid residue upstream the phosphorylatable serine or threonine which, upon phosphorylation of the peptide, is in proximity and orientation that accounts for a strong association with Phe93 of GSK-3, or an equivalent amino acid, as defined herein.

By "proximity and orientation" it is meant that, as discussed hereinabove, the amino acid of the peptide is sufficiently close and properly oriented so as to strongly interact with the amino acid within the catalytic domain of the enzyme.

By "interacting" or "interact", in the context of an amino acid of the peptide and an amino acid in the catalytic domain, it is meant a chemical interaction as a result of, for example, non-covalent interactions such as, but not limited to, hydrophobic interactions, including aromatic interactions, electrostatic interactions, Van der Waals interactions and hydrogen bonding. The interaction is such that results in the low dissociation constant of the phosphorylated peptide-enzyme complex as disclosed herein.

Since phenylalanine (as in Phe93) comprises a hydrophobic aromatic side chain (phenyl), in some embodiments, the interaction of the amino acid upstream the (previously phosphorylatable) serine or threonine residue in the phosphorylated peptide with the binding site of GSK-3 comprises hydrophobic interactions and/or aromatic interactions.

Thus, in some embodiments, the amino acid that interacts with Phe93 in GSK-3 so as to account for the low dissociation constant, is capable of binding to the aromatic side chain of Phe93 via hydrophobic and/or aromatic interactions.

Exemplary such amino acid residues which are suitable for being incorporated as the amino acid residue upstream the phosphorylatable serine or threonine residue in the peptide as described herein, include non-polar amino acid residues, non-charged amino acid residues (at a physiological pH), aromatic amino acid residues and hydrophobic amino acid residues.

Such amino acid residues include, but are not limited to, alanine, glycine, valine, leucine, isoleucine, proline, methionine, cysteine, tyrosine, tryptophan and phenylalanine. Non naturally-occurring amino acid residues which are characterized, for example, as hydrophobic or aromatic residues are also contemplated.

The term "hydrophobic", as used herein with reference to an amino acid or any other substance or moiety, describes a feature of the substance that renders its solubility in water lower than its solubility in hydrophobic organic solvents.

The term "hydrophobic" thus often translates into values such as Log P, which describes the partition coefficient of a substance between an aqueous phase (water) and an oily phase (1-octanol).

According to some embodiments of the present invention, a hydrophobic amino acid has a Log P value that is higher (i.e., less negative) than −3, or higher than −2.9, or higher than −2.8, or higher than −2.7, or higher than −2.6, or even higher than −2.5.

Exemplary hydrophobic amino acids include, but are not limited to, glycine, alanine, leucine, isoleucine, valine, proline, phenylalanine, methionine, cysteine and tryptophan.

In some embodiments, one of the amino acid residues upstream the phosphorylatable serine or threonine residue in the peptide (upstream Z residue in the recognition motif) is alanine, glycine, valine, leucine, isoleucine, proline, methionine, tyrosine, tryptophan or phenylalanine, and in some embodiments, one of these amino acid residues is alanine, glycine, valine, leucine, isoleucine or phenylalanine. In an exemplary embodiment, one of the amino acid residues upstream the phosphorylatable serine or threonine residue in the peptide (Z) is alanine.

In some of these embodiments, two or more of the amino acid residues upstream the phosphorylatable serine or threonine residue in the peptide (upstream Z residue in the recognition motif) are each independently alanine, glycine, valine, leucine, isoleucine, proline, methionine, cysteine, tyrosine, tryptophan or phenylalanine.

Alternatively, one of the amino acid residues upstream the phosphorylatable serine or threonine residue in the peptide (upstream Z residue in the recognition motif) is alanine, glycine, valine, leucine, isoleucine, proline, methionine, cysteine, tyrosine, tryptophan or phenylalanine and the other amino acid residues are each independently a polar amino acid residue or a charged amino acid residue.

Exemplary charged amino acids (which are charged at a physiological pH) include glutamic acid, aspartic acid, lysine, arginine and histidine. Non-naturally occurring amino acids with side chain that possesses carboxylic acid, amine, thiocarboxylic acid and the like, are also contemplated.

Exemplary polar amino acids include serine, threonine, asparagine and glutamine. Non-naturally occurring amino acids with side chain that possesses amide, thioamide, hydroxyl and the like, are also contemplated.

In some embodiments, one or more of the amino acid residues upstream the serine or threonine residue (upstream Z residue in the recognition motif) is a rigid amino acid residue.

By "rigid" it is meant an amino acid which possesses a rigid side chain, which is characterized by a low number of free rotations.

Exemplary rigid moieties include, but are not limited to, cyclic moieties, such as cycloalkyl, heteroalicyclic, aryl or heteroaryl, with aromatic cyclic moieties, aryls and heteroaryls, being more rigid then others and hence preferred. Such moieties further account for possible aromatic interactions with Phe93.

Exemplary rigid amino acid side chains include, but are not limited to, proline, histidine, tyrosine, tryptophane, and phenylalanine. Non-naturally occurring amino acid residues which possess side chain that comprises a rigid moiety as described herein are also contemplated.

In some embodiments, one or more of the amino acid residues upstream the phosphorylatable serine or threonine residue in the peptide is/are proline residues.

In some of these embodiments, the one or more proline residues are adjacent to the amino acid that interacts with the binding site.

The presence of such rigid amino acids may attribute to the interaction with the catalytic binding site since it may position the amino acid that interacts with the binding site at the proximity and orientation required for maximal interaction while restricting conformational changes that may reduce this interaction.

In any of the herein-described embodiments, the number of amino acid residues upstream the serine or threonine phosphorylatable residue ranges from 3 to 7.

In some embodiments, the amino acid residue which interacts with the amino acid residue within the GSK-3 binding domain (e.g, with Phe93) is at the third position upstream the serine or threonine phosphorylatable residue. This amino acid, however, can also be the first, second, fourth, fifth, sixth and/or seventh amino acid residue upstream the phosphorylatable serine or threonine residue, as long as the phosphorylated peptide arranges within the catalytic domain in such a configuration that brings this one or more amino acid residues to a proximity and orientation that enable it to interact with e.g., Phe93 of GSK-3 so as to result in the herein-described dissociation constant.

In any of the embodiments described herein, the peptide may further comprise one or more amino acid residues that are capable of interacting with other amino acid residues within the catalytic binding site of GSK-3.

In some embodiments, the peptide comprises one or more of a hydrophobic amino acid residue, as defined herein, which are suitably positioned with respect to other functional amino acid moieties so as to allow interactions with other subsites within the catalytic binding site of GSK-3 (e.g., the phosphate binding pocket).

Thus, in some embodiments, the peptide as described herein is such that is capable of interacting both with Phe93 of GSK-3 and with one or more additional amino acid residues within the catalytic binding site of a GSK-3 enzyme.

Any of the hitherto identified amino acid residues within the catalytic binding site of GSK-3 are contemplated, including, but not limited to, those described in Ilouz et al. (2006, supra), in Dajani et al. (supra) and in and in WO 2005/000192.

Thus, in addition to comprising an amino acid that is capable of interacting with Phe93, upon phosphorylation of the peptide, a peptide as disclosed herein further comprises moieties that are capable of interacting with one or more of such additional amino acid moieties. It is preferred that the moiety that is capable of interacting with Phe93 and the one or more additional moieties that are capable of interacting with other positions within the GSK-3 catalytic domain would be in a suitable proximity and orientation so as to allow mutual interactions with the different subsites within the catalytic binding site.

In some embodiments, an inhibitor as described herein is such that is capable of interacting, in addition to the Phe93, with the phosphate binding pocket of GSK-3, namely, with one or more of Arg86, Arg196 and Lys205.

In some embodiments, an inhibitor as described herein is such that is capable of interacting, in addition to Phe93, with a hydrophobic patch that is defined by Val214, I216 and Y216.

In some embodiments, the inhibitor as described herein is such that is capable of interacting both with Phe93 of GSK-3 and with one or more of the additional amino acids Phe67, Gln89, Asp90, Lys91, Arg92, Lys94 and Asp95 in the GSK-3 enzyme, or with one or more of Phe67, Gln89, Asp90, Arg92, Lys 94 and Asp95 in the GSK-3 enzyme, or with one or more of Phe67, Gln89 and Asn95.

Without being bound by any particular theory, it is assumed that a peptide as described herein interacts with GSK-3 similarly to a GSK-3 substrate, due to the presence of the recognition motif, yet, differently from the substrate, once the phosphorylatable serine or threonine residue in the recognition motif is phosphorylated, the peptide does not dissociate from the enzyme but rather remains interacted with the enzyme's binding site, presumably with Phe93 in the binding site.

It is assumed that upon the phosphorylation of the phosphorylatable serine or threonine residue, the obtained phosphorylated peptide undergoes conformational changes that bring one or more of the amino acid residues upstream the (previously phosphorylatable, and now phosphorylated) serine or threonine residues, to be in a proximity and orientation with respect to Phe93 (and/or any other amino acid residue in the GSK-3 catalytic binding site) such that this amino acid residue upstream the serine or threonine residue associates with the Phe93 residue and does not dissociates easily from the enzyme, thereby acting as an inhibitor.

Prediction and/or measurement of proximity and orientation can be performed, for example, by computational measurements, such as, for example, using construction of a model presenting a set of coordinates which represent the catalytic binding site of a GSK-3 enzyme as described herein.

In some of any of the embodiments described herein, the peptide as described herein can be sequenced after a known GSK-3 substrate or fragment thereof, while replacing one or more of the amino acid residues upstream the phosphorylatable serine or threonine residue in the recognition motif of the substrate (see, SEQ ID NO:1) with one or more amino acid residues that are capable of interacting with one or more amino acids in the catalytic binding site of the enzyme, so as to result in a dissociation constant that is much lower than that of the known substrate.

According to some embodiments of the present invention there is provided a peptide, having an amino acid sequence equivalent to an amino acid sequence of a known substrate of GSK-3 or a part of such a substrate, wherein the amino acid sequence comprises the $ZX_1X_2X_3Z(p)$ recognition motif (as set forth in SEQ ID NO:1) of a GSK-3 substrate, wherein Z(p) is a phosphorylated serine residue or a phosphorylated threonine residue; Z is a serine residue or threonine residue which is phosphorylatable by GSK-3, as described herein; and $X_1X_2X_3$ represent the corresponding amino acid residues of the known substrate, or, optionally, one or more of $X_1X_2X_3$ is different from the corresponding amino acid residues of the substrate.

In the herein disclosed peptides, an amino acid residue at a position upstream the phosphorylatable serine or threonine residue in the above-described recognition motif is different from an amino acid residue in a corresponding position in the known GSK-3 substrate.

Thus, the peptides disclosed herein may represent an amino acid sequence which is equivalent to an amino acid sequence of a known GSK-3 substrate and which introduces a substitution of an amino acid at a position which is outside the recognition motif of the amino acid sequence and is upstream this recognition motif.

According to some embodiments of the present invention, the peptides described herein can be considered as sequenced based on a natural or otherwise identified GSK-3 substrate (e.g., CREB or HSF-1, pCREB or pHSF-1), while maintaining the identified recognition motif of GSK-3 described hereinabove (see, SEQ ID NO:1), and while replacing one or more amino acids upstream of the phosphorylatable serine or threonine.

The phrase "natural GSK-3 substrate" or "known GSK-3 substrate" or "native GSK-3 substrate" or "identified GSK-3 substrate" (all being used herein interchangeably) describes any peptide (or protein) which is known to be phosphorylated by GSK-3 in a biological system. By "biological system" it is meant a system of any living species including, for example, vertebrates, poultry, mammals, human beings and microorganisms, including unicellular organisms.

Representative examples of natural GSK-3 substrates include, but are not limited to, HSF-1, GS-1 (glycogen synthase-1), insulin receptor substrate-1 (IRS-1), insulin receptor substrate-2 (IRS-2), cAMP responsive element binding protein (CREB), and phosphorylated peptides derived therefrom, such as, for example, pIRS-1 from the insulin receptor substrate-1 [see, for example, Liberman and Eldar-Finkelman (2005) supra], pHSF-1, p9CREB and pGS-1, some of which are set forth herein as having SEQ ID NOS: 3, and 45-55.

It is expected that during the life of a patent maturing from this application additional relevant GSK-substrates will be identified and the scope of the term "natural GSK-3 substrate" is intended to include all such new substrates a priori.

As discussed herein and is well-known in the art, GSK-3 substrates are phosphorylated at the (phosphorylatable) serine (or threonine) residue of the recognition motif, once the substrate interacts with the catalytic binding site of GSK-3.

Since the herein disclosed peptides also feature the GSK-3 recognition motif, it is assumed that once these peptides interact with the catalytic binding site of GSK-3, phosphorylation of the phosphorylatable serine (or threonine) residue in the recognition motif of the peptide is also effected, to thereby produce a phosphorylated peptide, in which the phosphorylatable serine of the recognition motif is now phosphorylated, so as to produce the amino acid sequence $Z(p)X_1X_2X_3Z(p)$ (SEQ ID NO:7) instead of the recognition motif sequence as set forth in SEQ ID NO:1.

In some embodiments, the amino acid residue upstream the serine residue of the recognition motif, which is different from the amino acid residue at a corresponding position of a known GSK-3 substrate, is such that when a phosphorylated peptide is formed upon interaction with the catalytic domain of GSK-3, as described herein, the phosphorylated peptide (which comprises the amino acid sequence $Z(p)X_1X_2X_3Z(p)$ as set forth in SEQ ID NO:7) interacts with a phenylalanine residue or an equivalent amino acid at position 93 of the GSK-3.

In some embodiments, the interaction of the phosphorylated peptide results in an increased association and hence in decreased dissociation constant of the to phosphorylated peptide, compared to the dissociation constant of the corresponding GSK-3 substrate.

Hence, in some embodiments, the substituting amino acid, namely, the amino acid upstream the phosphorylatable serine or threonine residue in the recognition motif, is selected such that upon phosphorylation of the peptide at the binding site of GSK-3, a dissociation constant of the phosphorylated peptide is lower by at least 2-folds, 5-folds, 10-folds or even by more, than a dissociation constant of the known GSK-3 substrate after which the peptide is sequenced.

In some of these embodiments, the lower dissociation constant is a result of improved interaction of the peptide with Phe93 of GSK-3, compared to its corresponding substrate, upon phosphorylation of the phosphorylatable serine or threonine residue.

In some embodiments, the peptide disclosed herein therefore has an amino acid sequence of a known substrate of GSK-3, excepting one or more amino acid(s) upstream the recognition motif (in both the peptide and the substrate). The substituting amino acid in the peptide is such that accounts for an improved interaction and hence reduced dissociation rate, with the catalytic binding site of GSK-3, preferably with an amino acid at position 93 of GSK-3.

In some embodiments, the amino acid residue which is different from a corresponding amino acid in the substrate is such that is capable of interacting with the amino acid residue at position 93 of GSK-3 (e.g., Phe 93) or with an analog thereof. Exemplary such amino acid residues include, but are not limited to, residues of alanine, glycine, valine, leucine, isoleucine, proline, methionine, cysteine, tyrosine, tryphtophane and phenylalanine.

It is noted herein that the currently most recognizable GSK-3 substrates all include at least one polar or charged amino acid residue upstream the phosphorylatable serine or threonine residue (Z) in the recognition motif.

The amino acid sequences of exemplary such known GSK-3 substrates are presented in Table A hereinbelow, with the relevant polar or charged amino acid residues upstream the phosphorylatable serine or threonine residues are underlined.

TABLE A

| SEQ ID NO: | Specific phosphorylation sequence | Substrate |
|---|---|---|
| 45 | RPASVPPSPSLSRHSSPHQSEDEE | Glycogen synthase |
| 46 | KRREILSRRPSYR | CREB |
| 47 | EGTMSRPASVDGS | IRS1 |
| 48 | SGSASASGSPSDPGF | IRS2 |
| 49 | SYLDSGIHSGATTTAPSLSGKG | B-Catenin |
| 50 | EEPPSPPQSPRVEEAS | HSF1 |
| 51 | LLNASGSTSTPAPSRTASFSESR | ATP-citrate lyase |
| 52 | AIFKPGFSPQPSRRGSESSEEVY | G subunit of phosphatase1 |
| 53 | DSEELDSRAGSPQLDDIKVF | eIF2B |
| 54 | GLMKIDEPSTPYHSMIGDDDDAY | Inhibitor-2 |

In some embodiments, the peptide is based on a recognition motif of a GSK-3 substrate as defined herein and was previously described (see, for example, WO 01/49709).

Excluded from the scope of these embodiments of the present invention are peptides already reported in the art as acting as GSK-3 inhibitors or substrates. These include, for example, substrate competitive inhibitors of GSK-3 inhibitors as described in Plotkin et al. (2003) *J. Pharmacol. Exp. Ther.*, 974-980], in Kaidanovich-Beilin & Eldar-Finkelman (2005) *J. Pharmacol. Exp. Ther.* 316:17-24; in Rao et al. (2007) *Diabetologia* 50, 452-60; Kim et al. (2006) *Neuron* 52, 981-96; in Chen et al. (2004) *Faseb J* 18, 1162-4; in Kaidanovich-Beilin et al. (2004) *Biol. Psychiatry.* 55:781-4; in Shapira et al. (2007) *Mol. Cell Neurosci.* 34, 571-7]; in Ilouz et al. (2006) *J. Biol. Chem.* 281, 30621-30]; in U.S. Pat. Nos. 6,780,625 and 7,378,432; in WO 2004/052404, WO 2005/000192, WO 01/49709, WO 2012/101599 and WO 2012/101601; in Liberman, Z. & Eldar-Finkelman, H. (2005) *J. Biol. Chem.* 280, 4422-8; in Liberman et al. (2008) *Am. J. Physiol. Endocrinol. Metab.* 294, E1169-77; and in Bertrand et al. (2003) *J. Mol. Biol.* 333, 393-407.

The peptides as described herein can be collectively represented by the amino acid sequence I as follows:

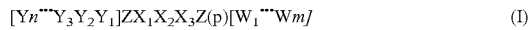

$$[Y_n\text{...}Y_3Y_2Y_1]ZX_1X_2X_3Z(p)[W_1\text{...}W_m] \quad (I)$$

wherein:
m equals 1, 2, 3, 4 or 5;
n is 3, 4, 5, 6 or 7, such that m and n are such that the peptide consists of no more than 15 amino acid residues;

Z(p) is the phosphorylated serine residue or said phosphorylated threonine residue;

Z is the phosphorylatable serine residue or the phosphorylatable threonine residue;

$X_1$, $X_2$, $X_3$, $Y_1$-$Y_n$ and $W_1$-$W_m$ are each independently any amino acid residue, wherein one or more of $Y_1$-$Y_n$ is/are selected so as to exhibit an interaction with the catalytic binding site of GSK-3 which is accountable for the low dissociation constant of the peptide, as described herein.

In some embodiments, $X_1$, $X_2$, $X_3$, $Y_1$-$Y_n$ and $W_1$-$W_m$ are the same as in a corresponding native GSK-3 substrate, as defined herein, except that one of $Y_1$-$Y_n$ is replaced by an amino acid residue that its interaction with the catalytic binding site of GSK-3 which is accountable for a dissociation constant of the peptide which is lower from that of the native GSK-3 substrate, as defined herein.

In some of any of the embodiments described herein, m, or the number of amino acids downstream the phosphorylated serine or threonine residue, equals 1 or 2.

In some of any of the embodiments described herein, the sum of n and m, or the number of amino acid residues in the peptide outside (both upstream and downstream) the recognition motif, is such that the peptide consists of 10 to 13 amino acid residues.

In some of any of the embodiments described herein, $Y_3$, or an amino acid residue at the third position upstream the Z residue in the recognition motif, is the amino acid residue that is different from a corresponding amino acid residue in the substrate and/or that upon phosphorylation of the peptide, its interaction with the binding site is accountable for the low dissociation constant.

In some of these embodiments, $Y_3$ can be, for example, a glycine residue, an alanine residue, a valine residue, a leucine residue, an isoleucine residue, a proline residue, a methionine residue, a cysteine residue, a tyrosine residue, a tryptophan residue or a phenylalanine residue. In some of these embodiments, $Y_3$ can be, for example, a glycine residue, an alanine residue, a valine residue, a leucine residue, an isoleucine residue or a phenylalanine residue. In some embodiments, $Y_3$ is an alanine residue.

In some of these embodiments, $Y_3$, or an amino acid residue at the third position upstream the Z residue in the recognition motif, is other than glutamic acid residue (Glu).

In some of these embodiments, $Y_3$, or an amino acid residue at the third position upstream the Z residue in the recognition motif, is other than any of the polar and charged amino acid residues as described herein.

In some of any of the embodiments described herein, the peptide as described herein is sequenced after the amino acid of the GSK-3 substrate HSF-1.

As delineated hereinabove, HSF-1 has an amino acid sequence as set forth in SEQ ID NO:3.

In some embodiments, the amino acid sequence of a peptide as described herein corresponds to the amino acid sequence of HSF-1, excepting the Glu residue at the third position upstream the phosphorylatable serine residue (the third amino acid residue in SEQ ID NO:3).

In some embodiments, the Glu residue of HSF-1 is replaced by alanine residue.

An exemplary such peptide comprises or consists of an amino acid sequence as set forth in SEQ ID NO:9 (FOR L-807).

In some of these embodiments, the peptide as described herein can be represented by the amino acid sequence II:

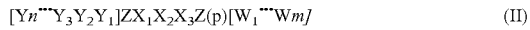

$$[Y_n\text{...}Y_3Y_2Y_1]ZX_1X_2X_3Z(p)[W_1\text{...}W_m] \quad (II)$$

wherein, n is 5, 6 or 7, m is 1, 2, 3, 4 or 5;

m and n are such that the peptide consists of no more than 15 amino acid residues;

Z(p) is a phosphorylated serine residue or a phosphorylated threonine residue;

Z is the phosphorylatable serine or threonine residue as described herein;

$X_1$, $X_2$, $X_3$ and $W_1$-Wm is each independently any amino acid residue; and $Y_1$-$Y_5$ is represented by an amino acid sequence having SEQ ID NO:8:

```
                                        (SEQ ID NO: 8)
Lys-Glu-Y₃-Pro-Pro
``` wherein $Y_3$ is any amino acid residue excepting a glutamic acid residue.

In some of these embodiments, $Y_3$ in amino acid sequence II above can be, for example, glycine residue, alanine residue, valine residue, leucine residue, isoleucine residue, or phenylalanine residue.

In some of these embodiments, $Y_3$ is an alanine residue.

In some of these embodiments, at least one of n, m, $X_1$, $X_2$, $X_3$ and $W_1$-Wm is identical to a corresponding amino acid residue of HSF-1.

In some of these embodiments, each of n, m, $X_1$, $X_2$, $X_3$ and $W_1$-Wm is identical to a corresponding amino acid residue of HSF-1.

In some of any of the embodiments of a peptide as described herein, Z in the recognition motif is a phosphorylatable serine residue.

In some of any of the embodiments of a peptide as described herein, Z(p) in the recognition motif is a phosphorylated serine residue.

In some of any of the embodiments of a peptide as described herein, at least one of $X_1$, $X_2$ and $X_3$ within the recognition motif of the peptide is a hydrophobic amino acid residue.

In some of any of the embodiments of a peptide as described herein, the amino acid residue at the first position upstream of the phosphorylated serine or threonine in the recognition motif (denoted as $X_3$) is a hydrophobic amino acid residue, as defined herein.

Thus, in some embodiments, the peptides described herein can be considered as sequenced based on a natural or otherwise identified GSK-3 substrate, while maintaining the identified recognition motif of GSK-3 described hereinabove (see, SEQ ID NO:1), which includes a phosphorylated serine or threonine residue and a phosphorylatable serine or threonine residue, while replacing an amino acid residue upstream of the phosphorylatable serine or threonine residue as described herein, and while further replacing the amino acid residue at the first position upstream of the phosphorylated serine or threonine by a hydrophobic amino acid residue, as defined herein.

In some embodiments, $X_3$ is a proline residue or an alanine residue.

In some embodiments, $X_3$ is a proline residue.

In some embodiments, $X_3$ is an amino acid that has a hydrophobic side chain which is rigid, thus ensuring better interaction (reduced entropy) with the catalytic binding site. Exemplary such amino acids have a side chain that comprises an aryl (e.g., tryptophane and phenylalanine) or a heteroaryl (e.g., proline).

$X_1$ and $X_2$ in the amino acid sequence of the peptide described herein can be any amino acid, as described herein.

In some embodiments, at least one, or both, of $X_1$ and $X_2$ is a hydrophobic amino acid, as described herein.

Thus, in some embodiments, each of $X_1$, $X_2$ and $X_3$ is a hydrophobic amino acid residue, as described herein (e.g., alanine or proline).

In some embodiments, $X_1$ and $X_2$ are each a proline residue.

In some embodiments, each of $X_1$, $X_2$ and $X_3$ is a proline residue.

In some embodiments, a peptide as described herein comprises any one of the following amino acid sequences as the moiety denoted as $ZX_1X_2X_3S(p)$ (the recognition motif) in amino acid sequence I, as non-limiting examples:

```
                                        (SEQ ID NO: 11)
Ser-Pro-Pro-Pro-phosphorylated serine (SEQ ID NO: 12)
Ser-Pro-Pro-Pro-phosphorylated threonine (SEQ ID NO: 13)
Ser-Ala-Pro-Pro-phosphorylated serine (SEQ ID NO: 14)
Ser-Ala-Pro-Pro-phosphorylated threonine (SEQ ID NO: 15)
Ser-Ala-Ala-Pro-phosphorylated serine (SEQ ID NO: 16)
Ser-Ala-Ala-Pro-phosphorylated threonine (SEQ ID NO: 17)
Ser-Pro-Ala-Pro-phosphorylated serine (SEQ ID NO: 18)
Ser-Pro-Ala-Pro-phosphorylated threonine (SEQ ID NO: 19)
Ser-Gly-Pro-Pro-phosphorylated serine (SEQ ID NO: 20)
Ser-Gly-Pro-Pro-phosphorylated threonine (SEQ ID NO: 21)
Ser-Gly-Gly-Pro-phosphorylated serine (SEQ ID NO: 22)
Ser-Gly-Gly-Pro-phosphorylated threonine (SEQ ID NO: 23)
Ser-Pro-Gly-Pro-phosphorylated serine (SEQ ID NO: 24)
Ser-Pro-Gly-Pro-phosphorylated threonine (SEQ ID NO: 25)
Ser-Leu/Ile-Pro-Pro-phosphorylated serine (SEQ ID NO: 26)
Ser-Leu/Ile-Pro-Pro-phosphorylated threonine (SEQ ID NO: 27)
Ser-Leu/Ile-Leu/Ile-Pro-phosphorylated serine (SEQ ID NO: 28)
Ser-Leu/Ile-Leu/Ile-Pro-phosphorylated threonine (SEQ ID NO: 29)
Ser-Pro-Leu/Ile-Pro-phosphorylated serine (SEQ ID NO: 30)
Ser-Pro-Leu/Ile-Pro-phosphorylated threonine
```

Ser-Val-Pro-Pro-phosphorylated serine (SEQ ID NO: 31)

Ser-Val-Pro-Pro-phosphorylated threonine (SEQ ID NO: 32)

Ser-Val-Val-Pro-phosphorylated serine (SEQ ID NO: 33)

Ser-Val-Val-Pro-phosphorylated threonine (SEQ ID NO: 34)

Ser-Pro-Val-Pro-phosphorylated serine (SEQ ID NO: 35)

Ser-Pro-Val-Pro-phosphorylated threonine. (SEQ ID NO: 36)

In some embodiments, in any of these moieties, the Pro residue at the first position upstream the phosphorylated serine or threonine ($X_3$) is replaced by any of the other hydrophobic moieties as described herein (e.g., Phe or Trp).

In alternative embodiments, the "Ser" residue of any of these moieties is replaced by a Thr residue.

It is to be noted that for $X_1$, $X_2$ and $X_3$, any combination of 3 hydrophobic amino acid residues as defined herein is contemplated in some embodiments of the present invention, and that any such combination can be combined with either a phosphorylated serine residue or a phosphorylated threonine residue at the position denoted Z(p), and with either a serine residue or a threonine residue at the position denoted Z.

In some embodiments, the number and nature of amino acid residues downstream the residue denoted as Z(p) and upstream the residue denoted as Z, is determined by the amino acid sequence of the GSK-3 substrate after which the peptide is designed.

In some embodiments, m is 1.

In some embodiments, $W_1$ is a proline residue, although any other amino acid residue at this position, and at position $W_2$ (if present, when m=2) is also contemplated.

In some embodiment, $W_1$ is a hydrophobic amino acid residue, as defined herein, and, for example, $W_1$ is phenylalanine.

In some embodiments, n is 5, such that the peptide comprises an amino acid sequence as described herein, in which upstream to Z there are amino acid residues denoted as $Y_1$-$Y_5$.

In some embodiments, when the peptide is designed after the substrate HSF-1, $Y_1$-$Y_5$ has the amino acid sequence Lys-Glu-$Y_3$-Pro-Pro, as set forth in any of SEQ ID NOS:8 and 37-42. However, any other sequence of amino acid residues can be included within the amino acid residues upstream to Z, as long as it is such that exhibits the herein described interactions with the GSK-3 binding site.

In some embodiments, $Y_1$-$Y_5$ has the amino acid sequence Lys-Glu-$Y_3$-Pro-Pro, as set forth in any of SEQ ID NOS:8 and 37-42; and the recognition motif $ZX_1X_2X_3Z(p)$ has any of the amino acid sequences as set forth in SEQ ID NOS:11-36.

According to some embodiments of the present invention, there are provided peptides corresponding to any one of the peptide inhibitors described herein, in which the phosphorylatable serine or threonine residue is phosphorylated.

In some of these embodiments, these peptides are collectively represented by as peptides having the amino acid sequence II*:

$[Yn\cdots Y_3Y_2Y_1]Z(p)_1X_2X_3Z(p)_2[W_1\cdots Wm]$ (II*)

wherein:

n is 5, 6 or 7, m is 1, 2, 3, 4 or 5;

m and n are such that the peptide consists of no more than 15 amino acid residues, as described herein;

$Z(p)_1$ and $Z(p)_2$ are each independently a phosphorylated serine residue or a phosphorylated threonine residue;

$X_1$, $X_2$, $X_3$ and $W_1$-Wm are each independently any amino acid residue, as described in any one of respective embodiments for peptides having amino acid sequence II; and $Y_1$-Yn comprises an amino acid sequence as set forth in SEQ ID NO:8:

Lys-Glu-$Y_3$-Pro-Pro (SEQ ID NO: 8)

wherein $Y_3$ is any amino acid residue excepting a glutamic acid residue, as described in any one of respective embodiments for peptides having amino acid sequence II.

In some embodiments, any one of the peptides described herein can further comprise a hydrophobic moiety covalently attached thereto.

As used herein the phrase "hydrophobic moiety" refers to any substance that is characterized by hydrophobicity, namely, its solubility in water is much lower than its solubility in hydrophobic organic solvents, as defined herein.

In some embodiments, any hydrophobic moiety that is structurally suitable for interacting with a hydrophobic patch within a GSK-3 dimer, can be attached to the polypeptide described above.

The hydrophobic patch has been previously described by Dajani et al. (2001, supra). The crystallization data of Dajani et al. showed that GSK-3 is crystallized as a dimer, suggesting that this dimerization has biological relevance. The catalytic region (residues 216-220) of one monomer (a) appears to interact with the N-terminus of an α-helix (residues 262-273) of the other monomer (b). This interaction of the two monomers (a) and (b) forms a hydrophobic patch in monomer (b).

Alternatively, or in addition, the hydrophobic moiety is selected such that it enhances cell permeability of the peptide. Enhanced cell permeability can be determined by any method known in the art, for example, by determining a cellular uptake in in vitro studies.

Representative examples of hydrophobic substances from which the hydrophobic moiety of the present invention can be derived include, without limitation, substituted and unsubstituted, saturated and unsaturated hydrocarbons, where the hydrocarbon can be an aliphatic, an alicyclic or an aromatic compound and preferably includes at least 4 carbon atoms, more preferably at least 8 carbon atoms, more preferably at least 10 carbon atoms. In some embodiments, the hydrocarbon bears a functional group which enables its attachment to an amino acid residue. Representative examples of such a functional group include, without limitation, a free carboxylic acid (C(=O)OH), a free amino group ($NH_2$), an ester group (C(=O)OR, where R is alkyl, cycloalkyl or aryl), an acyl halide group (C(=O)A, where A is fluoride, chloride, bromide or iodide), a halide (fluoride, chloride, bromide or iodide), a hydroxyl group (OH), a thiol group (SH), a nitrile group (C≡N), a free C-carbamic group (NR"—C(=O)—OR', where each of R' and R" is independently hydrogen, alkyl, cycloalkyl or aryl), a free N-carbamic group (OC(=O)—NR'—, where R' is as defined above), a thionyl group (S(=O)$_2$A, where A is halide as defined above) and the like.

In some embodiments, the hydrophobic moiety comprises one or more fatty acid(s).

Representative examples of fatty acids that are usable in the context of the present invention include, without limitation, saturated or unsaturated fatty acids that have more than 10 carbon atoms, preferably between 12 and 24 carbon atoms, such as, but not limited to, myristic acid, lauric acid, palmitic acid, stearic acid, oleic acid, linoleic acid, linolenic acid, arachidonic etc., with myristic acid being presently the most preferred.

The hydrophobic moiety according to some embodiments of the present invention can be a fatty acid, or derived from any other hydrophobic substance as described above, per se, such that the fatty acid, or any other hydrophobic substance, is covalently attached directly to an amino acid residue of the peptide (via, for example, en ester bond or an amide bond). Alternatively, the hydrophobic moiety can be an amino acid residue that is modified to include a fatty acid, or any other hydrophobic substance as described hereinabove, such that this modified amino acid residue is attached to the peptide via a peptide bond or a substituted peptide bond, as is described herein. Further alternatively, the hydrophobic moiety can be a short peptide in which one or more amino acid residues are modified to include a fatty acid or any other hydrophobic substance as described herein. Such a peptide preferably includes between 2 and 15 amino acid residues and is attached to the peptide via a peptide bond or a substituted peptide bond, as is described herein.

As an alternative to, or in combination with the hydrophobic moiety described above, the hydrophobic moiety, according to the present invention, can comprise a hydrophobic peptide sequence. The hydrophobic peptide sequence, according to the present invention, preferably includes between 2 and 15 amino acid residues, more preferably between 2 and 10 amino acid residues, more preferably between 2 and 5 amino acid residues, in which at least five consecutive amino acid residues are hydrophobic amino acid residues.

Alternatively, the hydrophobic amino acid residue can include any other amino acid residue, which has been modified by incorporation of a hydrophobic moiety thereto.

The hydrophobic moiety or moieties as described herein are preferably attached to one or more termini of the peptide, namely the N-terminus and/or the C-terminus of the polypeptide. In some embodiments, the hydrophobic moiety is attached, directly or indirectly, as described herein, to the N-terminus of the polypeptide.

An exemplary peptide has the amino acid sequence Myristic-Gly-Lys-Glu-Ala-Pro-Pro-Ser-Pro-Pro-Gln-phosphorylated Ser-Pro (SEQ ID NO:10; L807-mts).

It is to be noted that a dissociation constant as described herein can be determined either experimentally, as defined herein, or be predicted computationally, by methods known in the art.

Computational modeling can also be utilized, based on the structural features uncovered herein as required for providing a disease-selective substrate-competitive peptide inhibitor of GSK-3, for screening a library of peptides for a putative inhibitor of GSK-3.

Thus, according to an aspect of some embodiments of the present invention there is provided another method of identifying a putative substrate-competitive inhibitor of GSK-3. In some embodiments, this method is effected by computationally screening a plurality of peptides that possess a recognition motif as forth in SEQ ID NO:7 for a peptide capable of interacting with a Phe93 residue, or an equivalent amino acid thereof, within a set of atomic structural coordinates defining a three-dimensional atomic structure of a catalytic binding site of GSK-3 (e.g., a GSK-3 as set forth in SEQ ID NO:5).

In some embodiments, the method is effected by computationally screening a plurality of peptides comprising a recognition motif as forth in SEQ ID NO:7 (e.g., peptides having an amino acid sequence II* as described herein); and determining for each peptide in said plurality of peptides its capability to interact with a Phe93 residue, or an equivalent amino acid residue thereof, within a set of atomic structural coordinates defining a three-dimensional atomic structure of a catalytic binding site of GSK-3.

Those peptides capable of interacting with the Phe93 residue, or an equivalent amino acid residue thereof, are determined as capable of inhibiting an activity of GSK-3.

As described herein, such peptides are generated upon contacting a corresponding non-phosphorylated peptide, or a phosphorylatable peptide, with GSK-3, at the catalytic binding site of the enzyme.

Hence, upon determining the phosphorylated peptides which interact Phe93, a corresponding peptide, in which Z(p) in the amino acid sequence is replaced by Z as in SEQ ID NO:1, is identified as a putative substrate-competitive peptide inhibitor of GSK-3.

In some embodiments, the method is effected further by computationally screening a second plurality of peptides that possess a recognition motif as forth in SEQ ID NO:1, within a set of atomic structural coordinates defining a three-dimensional atomic structure of a catalytic binding site of GSK-3 (e.g., a GSK-3 as set forth in SEQ ID NO:5);

and identifying those peptides in the second plurality of peptides, which when not-phosphorylated, exhibit no interaction, or reduced interaction, compared to the first plurality of (phosphorylated) peptides, with a Phe93 residue, or an equivalent amino acid thereof, within a set of atomic structural coordinates defining a three-dimensional atomic structure of a catalytic binding site of GSK-3.

In some of these embodiments, the peptides in the second plurality of peptides are such that correspond to the peptides in the first plurality of peptides, but in which the Z(p) in the amino acid sequence is replaced by Z, as in SEQ ID NO:1. Thus, the peptides in the second plurality of peptides are "non-phosphorylated" peptides corresponding to the peptides in the first plurality of peptides.

In some embodiments, only (not-phosphorylated) peptides corresponding to the peptides in the first plurality of peptides, which were determined as capable of interacting with the Phe93 residue (or an equivalent amino acid residue thereof), are screened.

In some embodiments, the method is further effected by determining, for each peptide in the first plurality of peptides which is determined as capable of interacting with the Phe93 residue, an interaction of a corresponding peptide in which Z(p) in the amino acid sequence is replaced by Z as in SEQ ID NO:1, with the Phe93 residue, or an equivalent amino acid residue thereof, within the set of atomic structural coordinates defining a three-dimensional atomic structure of a catalytic binding site of GSK-3.

A corresponding peptide in the second plurality of peptides which exhibits no interaction or reduced interaction, compared to the peptide in the first plurality of peptides determined as capable of interacting with said Phe93 residue, is identified as a putative substrate-competitive peptide inhibitor of GSK-3.

In some embodiments, the method is further effected by identifying a peptide that is further capable, in addition to interacting with Phe93, of interacting with at least one additional amino acid within the catalytic binding site of a GSK-3.

In some embodiments, peptides in the first or second (preferably first) plurality of peptides which are determined as capable of interacting with Phe93 residue, or an equivalent amino acid residue thereof, are further screened for their capability of interacting with one or more amino acid residues within the catalytic binding site of a GSK-3.

Such peptides which further interact with one or more additional amino acid residue(s) within the catalytic binding site of the GSK-3 are identified as putative substrate-competitive inhibitors of GSK-3.

In some embodiments, the additional amino acid is one or more of Phe67, Gln89, Asp90, Lys91, Arg92, Lys94 and Asp95 in a GSK-3 enzyme (e.g., wild-type GSK-3 enzyme such as human GSK-3β).

In some embodiments, the additional amino acid is one or more of Phe67, Gln89, Asp90, Arg92, Lys 94 and Asp95 in a GSK-3 enzyme (e.g., wild-type GSK-3 enzyme such as human GSK-3β).

In some embodiments, the additional amino acid is one or more of Phe67, Gln89 and Asn95 (e.g., wild-type GSK-3 enzyme such as human GSK-3β).

In some embodiments, the additional amino acid is one or more of any of the amino acids identified hitherto with respect to substrate's binding in GSK-3, as delineated hereinabove.

The method of these embodiments of the present invention is generally effected by constructing a model using a set of atomic structural coordinates defining a three-dimensional atomic structure of GSK-3 and computationally screening the one or more pluralities of peptides, as described herein, for a phosphorylated peptide capable of interacting with Phe93, to thereby identify the GSK-3 inhibitor, as described herein.

Typically, obtaining the set of atomic coordinates which define the three dimensional structure of an enzyme can be effected using various approaches which are well known in the art.

Structural data obtained is preferably recorded on a computer readable medium so as to enable data manipulation and construction of computational models. As used herein, "computer readable medium" refers to any medium which can be read and accessed directly by a computer. Such media include, but are not limited to, magnetic storage media, such as floppy discs, hard disc storage medium, and magnetic tape; optical storage media such as optical discs or CD-ROM; electrical storage media such as RAM and ROM; and hybrids of these categories such as magnetic/optical storage media. Selection and use of appropriate storage media is well within the capabilities of one of ordinary skill in the art.

As used herein, "recorded" refers to a process of storing information on computer readable medium.

It will be appreciated that a number of data storage devices can be used for creating a computer readable medium having recorded thereon the structural data of the present invention. The choice of the data storage structure is typically based on the means chosen to access the stored information. In addition, a variety of data processor programs and formats can be used to store the data information of the present invention on computer readable medium. The sequence information can be represented in a word processing text file, formatted in commercially-available software such as WordPerfect and MICROSOFT Word, or represented in the form of an ASCII file, stored in a database application, such as DB2, Sybase, Oracle, or the like.

It will be appreciated that structure models are preferably generated by a computing platform, which generates a graphic output of the models via a display generating device such as screen or printer. The computing platform generates graphic representations of atomic structure models via a processing unit which processes structure coordinate data stored in a retrievable format in the data storage device.

Suitable software applications, well known to those of skill in the art, which may be used by the processing unit to process structure coordinate data so as to provide a graphic output of three-dimensional structure models generated therewith via display include, for example, RIBBONS (Carson, M., 1997. Methods in Enzymology 277, 25), O (Jones, T A. et al., 1991. Acta Crystallogr A47, 110), DINO (DINO: Visualizing Structural Biology (2001): www(dot)dino3d(dot)org); and QUANTA, CHARMM, INSIGHT, SYBYL, MACROMODE, ICM, MOLMOL, RASMOL and GRASP (reviewed in Kraulis, J., 1991. Appl Crystallogr. 24, 946).

As mentioned hereinabove, once a structural model of GSK-1 is obtained substances which specifically bind the Phe93 residue in the active site of the model are identifiable. This is preferably effected using Rational Drug Design (RDD).

One approach to identify a putative inhibitor via rational drug design is by screening a peptide structure database ("3D database"), using software employing "scanner" type algorithms. Such software applications utilize atomic coordinates defining the three-dimensional structure of a binding pocket of a molecule and of a chemical structure stored in the database to computationally model the "docking" of the screened chemical structure with the binding pocket so as to qualify the binding of the binding pocket, or of the indicated amino acid therein, with the chemical structure. Iterating this process with each of a plurality of chemical structures stored in the database therefore enables computational screening of such a plurality to identify a chemical structure potentially having a desired binding interaction with the binding pocket, or with the indicated amino acid residue therein, and hence the putative inhibitor.

Any commercially available library of peptides can be used as a suitable chemical structure database for identifying the inhibitor as described herein.

Alternatively, identifying the inhibitor can be effected using de novo rational drug design, or via modification of a known chemical structure. In such case, software comprising "builder" type algorithms utilizes a set of atomic coordinates defining a three-dimensional structure of the binding pocket and the three-dimensional structures of basic chemical building blocks to computationally assemble a putative inhibitor. Such an approach may be employed to structurally refine a putative inhibitor identified, for example, via peptide database screening as described above.

Ample guidance for performing rational drug design by utilizing software employing such "scanner" and "builder" type algorithms is available in the literature.

Criteria employed by software programs used in rational drug design to qualify the binding of screened chemical structures with binding pockets include gap space, hydrogen bonding, electrostatic interactions, van der Waals forces, hydrophilicity/hydrophobicity, etc. Generally, the greater the contact area between the screened substance and the indicated binding site of the enzyme, the lower the steric hindrance, the lower the "gap space", and the greater the number of at least the hydrophobic interactions, the greater will be the capacity of the screened substance to bind to the indicated amino acid residue within the binding site of GSK-3.

The "gap space" refers to unoccupied space between the van der Waals surface of a screened substance positioned within a binding pocket and the surface of the binding pocket defined by amino acid residues in the binding pocket. Gap space may be identified, for example, using an algorithm based on a series of cubic grids surrounding the docked molecule.

Modeling or docking may be followed by energy minimization with standard molecular mechanics force fields or dynamics with programs known in the art.

In some embodiments, once a putative substance is identified in silico, it is further tested by "wet" experiments, by determining, in vitro, an inhibition of an activity of GSK-3 by the substance, as described herein.

In some embodiments, in order to further substantiate that the substance is an effective substrate-competitive inhibitor, its binding to Phe93 is determined by comparing an inhibition of an activity of a wild-type GSK-3 to an inhibition of an activity of a mutated GSK-3 that comprises an amino acid substitution with respect to Phe93 (e.g., as set forth in SEQ ID NO:6), as described herein.

Thus, a substance that (i) is in silico identified suitable to bind Phe93 in a GSK-3 enzyme; (ii) inhibits an activity of GSK-3 in in vitro assays for determining a kinase activity in the presence and absence of the substance; and (iii) inhibits an activity of a Phe93-mutated GSK-3 enzyme by less than 20%, is identified as a putative (potent) GSK-3 substrate competitive inhibitor. Further according to embodiments of the present invention, there is provided a process of preparing any of the peptides as described herein.

In one embodiment, the peptide of the present invention is prepared by a chemical synthesis, using well known chemical procedures, such as solution or solid-phase peptide synthesis, or semi-synthesis in solution. The peptide can be chemically synthesized, for example, by the solid phase peptide synthesis of Merrifield et al (1964). Alternatively, a peptide can be synthesized using standard solution methods (see, for example, Bodanszky, 1984). Newly synthesized peptides can be purified, for example, by high performance liquid chromatography (HPLC), and can be characterized using, for example, mass spectrometry or amino acid sequence analysis.

Alternatively, the peptides of the invention can be provided recombinantly. Systems for cloning and expressing the peptide include various microorganisms and cells that are well known in recombinant technology. These include, for example, various strains of *E. coli, Bacillus, Streptomyces*, and *Saccharomyces*, as well as mammalian, yeast and insect cells. The peptide can be produced as a peptide or fusion protein (e.g., tagged peptide). Suitable vectors for producing the peptide are known and available from private and public laboratories and depositories and from commercial vendors. See Sambrook et al, (1989). Recipient cells capable of expressing the gene product are then transfected. The transfected recipient cells are cultured under conditions that permit expression of the recombinant gene products, which are recovered from the culture. Host mammalian cells, such as Chinese Hamster ovary cells (CHO) or COS-1 cells, can be used. These hosts can be used in connection with poxvirus vectors, such as vaccinia or swinepox. Suitable non-pathogenic viruses that can be engineered to carry the synthetic gene into the cells of the host include poxviruses, such as vaccinia, adenovirus, retroviruses and the like. A number of such non-pathogenic viruses are commonly used for human gene therapy, and as carrier for other vaccine agents, and are known and selectable by one of skill in the art. The selection of other suitable host cells and methods for transformation, culture, amplification, screening and product production and purification can be performed by one of skill in the art by reference to known techniques (see, e.g., Gething et al, 1981).

Once the peptide is provided, a hydrophobic moiety or moieties can be conjugated thereto, if desired, by commonly used techniques. For example, in cases where the hydrophobic moiety is a fatty acid, techniques for adding a fatty acid (e.g., myristic acid) to an amino acid residue within the peptide sequence are used. Alternatively, an amino acid residue is modified to include a hydrophobic moiety such as fatty acid and is thereafter attached to the peptide by known chemical procedures, as is described hereinabove.

In cases where the hydrophobic moiety comprises a hydrophobic peptide sequence, the hydrophobic peptide can be prepared using the methods described hereinabove and thereafter be conjugated to the polypeptide. Alternatively, the conjugate can be prepared recombinantly, using systems, as described hereinabove, for cloning and expressing a fused polypeptide that comprises the peptide as described herein and such a hydrophobic peptide sequence.

As is demonstrated in the Examples section that follows, exemplary peptides according to some embodiments of the present invention exhibit high inhibitory effect toward GSK-3.

As is discussed hereinabove, these peptides are characterized by specificity towards GSK-3, a specificity which is derived from the unique recognition motif of GSK-3, which, unlike other kinases, includes a phosphorylated serine or threonine residue, and the fact that the sequence of the peptide portion thereof is based on this recognition motif.

Hence, according to another aspect of some embodiments of the present invention, there is provided a method of inhibiting an activity of GSK-3, which is effected by contacting cells expressing GSK-3 with an effective amount of any of the peptides described herein (e.g., represented by amino acid sequence I).

As used herein, the term "effective amount" is the amount determined by such considerations as are known in the art, which is sufficient to reduce the activity of GSK-3 by at least 5%, at least 10%, at least 20%, at least 50% and even at least 80%, 90% or by 100%. Typical assays for measuring kinase activity can be used for determining the inhibitory activity of the peptides as described herein.

As is demonstrated in the Examples section that follows, a representative example of a peptide according to some embodiments of the present invention strongly inhibits GSK-3, with an $IC_{50}$ value of less than 50 μM, and even less than 1 μM, as measured by in vitro kinase assay.

Hence, the effective amount of a peptide as described herein can range from about 0.1 micromolar to about 100 micromolar, or from about 0.1 micromolar and about 50 micromolar, or from about 0.1 micromolar to about 20 micromolar, or from about 1 micromolar to about 20 micromolar, including any intermediate value between the indicated ranges.

As used herein throughout the term "about" refers to ±10%.

The method according to this aspect of the present invention can be effected by contacting the cells with the described peptides in vitro, ex vivo and in vivo.

Cells expressing GSK-3 can be derived from any biological sample, including, but not limited to, cell cultures or extracts thereof, enzyme preparations suitable for in vitro assays, biopsied material obtained from a mammal or extracts thereof, and samples of blood, saliva, urine, feces, semen, tears, spinal fluid, and any other fluids or extracts thereof.

In some embodiments, the method according to these embodiments, utilizes the peptides as described herein as active agents in biological assays, and in particular, as GSK-3 (substrate competitive) inhibitors in such assays.

The method according to these embodiments of the present invention preferably pertains to inhibition of the phosphorylation and/or autophosphorylation activity of GSK-3. In some embodiments, the activity is phosphorylation activity.

The method according to these embodiments of the present invention can be further effected by contacting the cells with an additional active ingredient that is capable of altering an activity of GSK-3, as is detailed hereinbelow.

The inhibition of GSK-3 activity is a way to increase insulin activity in vivo. High activity of GSK-3 impairs insulin action in intact cells. This impairment results from the phosphorylation of insulin receptor substrate-1 (IRS-1) serine residues by GSK-3. Studies performed in patients with type II diabetes (non-insulin dependent diabetes mellitus, NIDDM) show that glycogen synthase activity is markedly decreased in these patients, and that decreased activation of protein kinase B (PKB), an upstream regulator of GSK-3, by insulin is also detected. Mice susceptible to high fat diet-induced diabetes and obesity have significantly increased GSK-3 activity in epididymal fat tissue. Increased GSK-3 activity expressed in cells resulted in suppression of glycogen synthase activity.

Inhibition of GSK-3 activity therefore provides a useful method for increasing insulin activity in insulin-dependent conditions. For example, treatment with the peptides as described herein can result in improved glucose uptake and/or glucose tolerance.

Thus, according to another aspect of the present invention there is provided a method of potentiating insulin signaling, which is effected by contacting insulin responsive cells with an effective amount, as is defined hereinabove, of the peptide as described herein.

Contacting can be effected in vitro; as described herein, for example, by contacting a biological sample as described herein with one or more of the peptides described herein, or ex vivo, or in vivo, by administering a peptide as described herein to a patient in need thereof.

As used herein, the phrase "potentiating insulin signaling" includes an increase in the phosphorylation of insulin receptor downstream components and an increase in the rate of glucose uptake as compared with glucose uptake in untreated subjects or cells.

Potentiation of insulin signaling, in vivo, resulting from administration of the peptides as described herein, can be monitored as a clinical endpoint. In principle, the easiest way to look at insulin potentiation in a patient is to perform the glucose tolerance test. After fasting, glucose is given to a patient and the rate of the disappearance of glucose from blood circulation (namely glucose uptake by cells) is measured by assays well known in the art. Slow rate (as compared to healthy subject) of glucose clearance will indicate insulin resistance. The administration of a GSK-3 inhibitor such as the peptides described herein to an insulin-resistant patient increases the rate of glucose uptake as compared with a non-treated patient. The peptide may be administered to the patient for a longer period of time, and the levels of insulin, glucose, and leptin in blood circulation (which are usually high) may be determined. Decrease in glucose levels will indicate that the peptide potentiated insulin action. A decrease in insulin and leptin levels alone may not necessarily indicate potentiation of insulin action, but rather will indicate improvement of the disease condition by other mechanisms.

By inhibiting GSK-3 activity and/or potentiating insulin signaling, the peptides described herein may be effectively utilized for treating any biological condition that is associated with GSK-3.

Hence, according to another aspect of some embodiments of the present invention, there is provided a method of treating a biological condition associated with GSK-3 activity. The method, according to this aspect of the present invention, is effected by administering to a subject in need thereof a therapeutically effective amount of the peptide as described herein.

The phrase "biological condition associated with GSK-3 activity" as used herein includes any biological or medical condition or disorder in which effective GSK-3 activity is identified, whether at normal or abnormal levels. The condition or disorder may be caused by the GSK-3 activity or may simply be characterized by GSK-3 activity. That the condition is associated with GSK-3 activity means that some aspects of the condition can be traced to the GSK-3 activity. Such a biological condition can also be regarded as a biological or medical condition mediated by GSK-3.

Herein, the term "treating" includes abrogating, substantially inhibiting, slowing or reversing the progression of a condition or disorder, substantially ameliorating clinical symptoms of a condition or disorder or substantially preventing the appearance of clinical symptoms of a condition or disorder. These effects may be manifested, for non-limiting examples, by a decrease in the rate of glucose uptake with respect to type II diabetes or by halting neuronal cell death with respect to neurodegenerative disorders, as is detailed hereinbelow.

The term "administering" as used herein describes a method for bringing a peptide as described herein and cells affected by the condition or disorder together in such a manner that the peptide can affect the GSK-3 activity in these cells. The peptides described herein can be administered via any route that is medically acceptable. The route of administration can depend on the disease, condition, organ or injury being treated. Possible administration routes include injections, by parenteral routes, such as intravascular, intravenous, intra-arterial, subcutaneous, intramuscular, intratumor, intraperitoneal, intraventricular, intraepidural, intracerebroventicular, intranasal or others, as well as via oral, nasal, ophthalmic, rectal or topical routes of administration, or by inhalation. Sustained release administration is also encompassed herein, by means such as, for example, depot injections or erodible implants, or by sustained release oral formulations (e.g., solid oral formulations). Administration can also be intra-articularly, intrarectally, intraperitoneally, intramuscularly, subcutaneously, or by aerosol inhalant. Where treatment is systemic, the peptide can be administered orally, nasally or parenterally, such as intravenously, intramuscularly, subcutaneously, intraorbitally, intracapsularly, intraperitoneally or intracisternally, as long as provided in a composition suitable for effecting the introduction of the peptide into target cells, as is detailed hereinbelow.

In some embodiments, administration is effected nasally, namely via a nasal route of administration. A nasal administration can be effected either by intranasal injection or by means of a spray or liquid formulation that is administered nasally.

The phrase "therapeutically effective amount", as used herein, describes an amount administered to an individual, which is sufficient to abrogate, substantially inhibit, slow or reverse the progression of a condition associated with GSK-3 activity, to substantially ameliorate clinical symptoms of a such a condition or substantially prevent the appearance of clinical symptoms of such a condition. The GSK-3 activity can be a GSK-3 kinase activity. The inhibitory amount may be determined directly by measuring the inhibition of a GSK-3 activity, or, for example, where the desired effect is an effect on an activity downstream of GSK-3 activity in a pathway that includes GSK-3, the inhibition may be measured by measuring a downstream effect. Thus, for example where inhibition of GSK-3 results in the arrest of phosphorylation of glycogen synthase, the effects of the peptide may include effects on an insulin-dependent or insulin-related pathway, and the peptide may be administered to the point where glucose uptake is increased to optimal levels. Also, where the inhibition of GSK-3 results in the absence of phosphorylation of a protein that is required for further biological activity, for example, the tau protein, then the peptide may be administered until polymerization of phosphorylated tau protein is substantially arrested. Levels of hippocampous β-catenin are also indicative for an effect on GSK-3 activity. Therefore, the inhibition of GSK-3 activity will depend in part on the nature of the inhibited pathway or process that involves GSK-3 activity, and on the effects that inhibition of GSK-3 activity has in a given biological context.

The amount of the peptide that will constitute an inhibitory amount will vary depending on such parameters as the peptide and its potency, the half-life of the peptide in the body, the rate of progression of the disease or biological condition being treated, the responsiveness of the condition to the dose of treatment or pattern of administration, the formulation, the attending physician's assessment of the medical situation, and other relevant factors, and in general the health of the patient, and other considerations such as prior administration of other therapeutics, or co-administration of any therapeutic that will have an effect on the inhibitory activity of the peptide or that will have an effect on GSK-3 activity, or a pathway mediated by GSK-3 activity.

Although it is expected that the inhibitory amount will fall in a relatively broad range that can be determined through routine trials, an exemplary therapeutically effective amount according to the present invention is selected so as to achieve, at the treated site, an amount of the peptide that ranges between about 10 nmol and about 1000 nmol, or between about 10 nmol and about 500 nmol, or between about 100 nmol and about 400 nmol.

As is discussed in detail hereinabove, GSK-3 is involved in various biological pathways and hence, the method according to this aspect of the present invention can be used in the treatment of a variety of biological conditions, as is detailed hereinunder.

GSK-3 is involved in the insulin signaling pathway and therefore, in one example, the method according this aspect of the present invention can be used to treat any insulin-dependent condition.

By "insulin-dependent condition" it is meant any condition that is mediated by insulin and which is manifested or caused by reduced level of insulin or impaired insulin potentiation pathway. Exemplary such conditions include, but are not limited to, conditions that involve glucose intolerance and impaired glucose uptake, such as diabetes, including, for example, insulin-dependent diabetes and juvenile diabetes.

As GSK-3 inhibitors are known to inhibit differentiation of pre-adipocytes into adipocytes, in another example, the method of this aspect of the present invention can be used to treat obesity.

In yet another example, the method according to this aspect of the present invention can be used to treat diabetes including non-insulin dependent diabetes mellitus.

Diabetes mellitus is a heterogeneous primary disorder of carbohydrate metabolism with multiple etiologic factors that generally involve insulin deficiency or insulin resistance or both. Type I, juvenile onset, insulin-dependent diabetes mellitus, is present in patients with little or no endogenous insulin secretory capacity. These patients develop extreme hyperglycemia and are entirely dependent on exogenous insulin therapy for immediate survival. Type II, or adult onset, or non-insulin-dependent diabetes mellitus, occurs in patients who retain some endogenous insulin secretory capacity, but the great majority of them are both insulin deficient and insulin resistant. Approximately 95% of all diabetic patients in the United States have non-insulin dependent, Type II diabetes mellitus (NIDDM), and, therefore, this is the form of diabetes that accounts for the great majority of medical problems. Insulin resistance is an underlying characteristic feature of NIDDM and this metabolic defect leads to the diabetic syndrome. Insulin resistance can be due to insufficient insulin receptor expression, reduced insulin-binding affinity, or any abnormality at any step along the insulin signaling pathway (see U.S. Pat. No. 5,861,266).

The peptides described herein can be used to treat type II diabetes in a patient with type II diabetes as follows: a therapeutically effective amount of the peptide is administered to the patient, and clinical markers, e.g., blood sugar level, are monitored. The peptide can further be used to prevent type II diabetes in a subject as follows: a prophylactically effective amount of the peptide is administered to the patient, and a clinical marker, for example IRS-1 phosphorylation, is monitored.

Treatment of diabetes is determined by standard medical methods. A goal of diabetes treatment is to bring sugar levels down to as close to normal as is safely possible. Commonly set goals are 80-120 milligrams per deciliter (mg/dl) before meals and 100-140 mg/dl at bedtime. A particular physician may set different targets for the patent, depending on other factors, such as how often the patient has low blood sugar reactions. Useful medical tests include tests on the patient's blood and urine to determine blood sugar level, tests for glycated hemoglobin level (HbA$_{1c}$; a measure of average blood glucose levels over the past 2-3 months, normal range being 4-6%), tests for cholesterol and fat levels, and tests for urine protein level. Such tests are standard tests known to those of skill in the art (see, for example, American Diabetes Association, 1998). A successful treatment program can also be determined by having fewer patients in the program with diabetic eye disease, kidney disease, or nerve disease.

Hence, in one particular embodiment of the method according to this aspect of the present invention, there is provided a method of treating non-insulin dependent diabetes mellitus: a patient is diagnosed in the early stages of non-insulin dependent diabetes mellitus. A peptide as described herein is formulated in an enteric capsule. The patient is directed to take one tablet after each meal for the purpose of stimulating the insulin signaling pathway, and thereby controlling glucose metabolism to levels that obviate the need for administration of exogenous insulin.

In another example, the method according to these embodiments of the present invention can be used to treat affective disorders such as unipolar disorders (e.g., depression) and bipolar disorders (e.g., manic depression). As is demonstrated herein, the effect of the peptides as described herein was exemplified on up-regulation of β-catenin levels, thus indicating, a role of these GSK-3 inhibitors in the treatment of affective disorders.

As GSK-3 is also considered to be an important player in the pathogenesis of neurodegenerative disorders and diseases, the method according to this aspect of the present invention can be further used to treat a variety of such disorders and diseases.

In one example, since inhibition of GSK-3 results in halting neuronal cell death, the method according to these embodiments of the present invention can be used to treat a neurodegenerative disorder that results from an event that cause neuronal cell death. Such an event can be, for example, cerebral ischemia, stroke, traumatic brain injury or bacterial infection.

In another example, since GSK-3 activity is implicated in various central nervous system disorders and neurodegenerative diseases, the method according to these embodiments can be used to treat various chronic neurodegenerative diseases such as, but not limited to, Alzheimer's disease, Huntington's disease, Parkinson's disease, AIDS associated dementia, amyotrophic lateral sclerosis (AML) and multiple sclerosis.

As is discussed hereinabove, GSK-3 activity has particularly been implicated in the pathogenesis of Alzheimer's disease. Hence, in one representative embodiment of the method described herein, there is provided a method of treating a patient with Alzheimer's disease: A patient diagnosed with Alzheimer's disease is administered with a peptide as described herein, which inhibits GSK-3-mediated tau hyperphosphorylation, prepared in a formulation that crosses the blood brain barrier (BBB). The patient is monitored for tau phosphorylated polymers by periodic analysis of proteins isolated from the patient's brain cells for the presence of phosphorylated forms of tau on an SDS-PAGE gel known to characterize the presence of and progression of the disease. The dosage of the peptide is adjusted as necessary to reduce the presence of the phosphorylated forms of tau protein.

GSK-3 has also been implicated with respect to psychotic disorders such as schizophrenia, and therefore the method according to this aspect of embodiments of the present invention can be further used to treat psychotic diseases or disorders, such as schizophrenia.

GSK-3 has also been implicated with respect to affective disorders. Therefore, in another example, the method according to this aspect of the present invention can be used to treat affective disorders such as unipolar disorders (e.g., depression) and bipolar disorders (e.g., manic depression).

It should be noted that the peptides described herein are particularly advantageous in the treatment of psychotic, affective and neurodegenerative diseases or disorders since, apart from exerting enhanced inhibition activity of GSK-3, it is postulated that the inclusion of multiple hydrophobic amino acid residues within the peptides further provides for enhanced lipophilicity of the peptides and, as a result, for enhanced permeability through the blood brain barrier (BBB). This enhanced permeability may allow a systemic, rather than local, administration of the peptides, such that the need to administer the inhibitors intracerebroventricularly (icy) is avoided.

GSK-3 has also been implicated with respect to cardiovascular conditions, and therefore, the peptides described herein can be further used to treat cardiovascular diseases or disorders.

Cardiovascular diseases and disorders include, but are not limited to, atherosclerosis, a cardiac valvular disease, stenosis, restenosis, in-stent-stenosis, myocardial infarction, coronary arterial disease, acute coronary syndromes, congestive heart failure, angina pectoris, myocardial ischemia, thrombosis, Wegener's granulomatosis, Takayasu's arteritis, Kawasaki syndrome, anti-factor VIII autoimmune disease or disorder, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity, Chagas' disease or disorder, and anti-helper T lymphocyte autoimmunity.

GSK-3 has also been implicated with respect to conditions (e.g., infections) associated with pathogenic parasites (e.g., malaria and trypanosomiasis), and therefore, the peptides described herein can be further used to treat a condition (e.g, infection) that is associated with a presence of a pathogenic parasite in a subject. Exemplary parasites include *Acanthamoeba, Anisakis, Ascaris lumbricoides*, Botfly, *Balantidium coli*, Bedbug, Cestoda (tapeworm), Chiggers, *Cochliomyia hominivorax, Entamoeba histolytica, Fasciola hepatica, Giardia lamblia*, Hookworm, *Leishmania, Linguatula serrata*, Liver fluke, *Loa loa, Paragonimus*—lung fluke, Pinworm, *Schistosoma, Strongyloides stercoralis*, Mites, Tapeworm, *Toxoplasma gondii, Trypanosoma*, Whipworm, *Wuchereria bancrofti* and *Plasmodium falciparum* and related malaria-causing protozoan parasites.

Exemplary conditions caused by pathogenic parasites include, but are not limited to, *Acanthamoeba keratitis*, Amoebiasis, Ascariasis, Babesiosis, Balantidiasis, Baylisascariasis, Chagas disease, Clonorchiasis, *Cochliomyia*, Cryptosporidiosis, Diphyllobothriasis, Dracunculiasis (caused by the Guinea worm), Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Malaria, Metagonimiasis, Myiasis, Onchocerciasis, Pediculosis, Scabies, Schistosomiasis, Sleeping sickness, Strongyloidiasis, Taeniasis (cause of Cysticercosis), Toxocariasis, Toxoplasmosis, Trichinosis and Trichuriasis.

GSK-3 has also been suggested to be involved in stem cell maintenance and/or differentiation. Accordingly, the peptides described herein can be further utilized in the treatment of conditions in which transplantation of stem cells is used as part of the treatment. Such conditions include, for example, cancer and damaged tissues (treatable by tissue regeneration).

In some embodiments, the peptides described herein can be utilized for maintaining and/or differentiating stem cells. Thus, in some embodiments, there is provided a method of maintaining and/or differentiating stem cells, which is effected by contacting a peptide as described herein with stem cells. In some embodiments, the contacting is effected ex-vivo. In some embodiments, the contacting is effected in the presence of a physiological medium, as acceptable for stem cells preparations. In some embodiments, the contacting is effected by placing stem cells in a suitable medium which further comprises a peptide as described herein.

The method according to this aspect of the present invention can be further effected by co-administering to the subject one or more additional active ingredient(s) which is capable of altering an activity of GSK-3.

As used herein, "co-administering" describes administration of a peptide as described herein in combination with the additional active ingredient(s) (also referred to herein as active or therapeutic agent). The additional active agent can be any therapeutic agent useful for treatment of the patient's condition. The co-administration may be simultaneous, for example, by administering a mixture of the peptide and the additional therapeutic agent, or may be accomplished by administration of the peptide and the active agent separately, such as within a short time period. Co-administration also includes successive administration of the peptide and one or more of another therapeutic agent. The additional therapeutic agent or agents may be administered before or after the peptide. Dosage treatment may be a single dose schedule or a multiple dose schedule.

An example of an additional active agent is insulin.

Preferably, the additional active agent is capable of inhibiting an activity of GSK-3, such that the additional active agent can be any GSK-3 inhibitor other than the peptides described herein, and thus can be, as non-limiting examples, lithium, valproic acid and other peptides or small molecules that are shown to inhibit GSK-3 activity as described herein.

Alternatively, the additional active agent can be an agent that is capable of downregulating an expression of GSK-3.

An agent that downregulates GSK-3 expression refers to any agent which affects GSK-3 synthesis (decelerates) or degradation (accelerates) either at the level of the mRNA or at the level of the protein. For example, a small interfering polynucleotide molecule which is designed to downregulate the expression of GSK-3 can be used as an additional active agent according to some embodiments of the present invention.

An example for a small interfering polynucleotide molecule which can downregulate the expression of GSK-3 is a small interfering RNA or siRNA, such as, for example, the morpholino antisense oligonucleotides described by in Munshi et al. (Munshi C B, Graeff R, Lee H C, *J Biol Chem* 2002 Dec. 20; 277(51):49453-8), which includes duplex oligonucleotides which direct sequence specific degradation of mRNA through the previously described mechanism of RNA interference (RNAi) (Hutvagner and Zamore (2002) Curr. Opin. Genetics and Development 12:225-232).

As used herein, the phrase "duplex oligonucleotide" refers to an oligonucleotide structure or mimetics thereof, which is formed by either a single self-complementary nucleic acid strand or by at least two complementary nucleic acid strands. The "duplex oligonucleotide" of the present invention can be composed of double-stranded RNA (dsRNA), a DNA-RNA hybrid, single-stranded RNA (ssRNA), isolated RNA (i.e., partially purified RNA, essentially pure RNA), synthetic RNA and recombinantly produced RNA.

Preferably, the specific small interfering duplex oligonucleotide of the present invention is an oligoribonucleotide composed mainly of ribonucleic acids.

Instructions for generation of duplex oligonucleotides capable of mediating RNA interference are provided in www(dot)ambion(dot)com.

Hence, the small interfering polynucleotide molecule according to some embodiments of the present invention can be an RNAi molecule (RNA interference molecule).

Alternatively, a small interfering polynucleotide molecule can be an oligonucleotide such as a GSK-3-specific antisense molecule or a rybozyme molecule, further described hereinunder.

Antisense molecules are oligonucleotides, which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target polynucleotide. An additional region of the oligonucleotide may serve as a substrate for enzymes capable of cleaving RNA: DNA or RNA:RNA hybrids. An example for such includes RNase H, which is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

The antisense molecules of the present invention may be formed as composite structures of two or more oligonucleotides, modified oligonucleotides, as described above. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein fully incorporated by reference.

Rybozyme molecules are being increasingly used for the sequence-specific inhibition of gene expression by the cleavage of mRNAs. Several rybozyme sequences can be fused to the oligonucleotides of the present invention. These sequences include but are not limited ANGIOZYME specifically inhibiting formation of the VEGF-R (Vascular Endothelial Growth Factor receptor), a key component in the angiogenesis pathway, and HEPTAZYME, a rybozyme designed to selectively destroy Hepatitis C Virus (HCV) RNA, (Rybozyme Pharmaceuticals, Incorporated—WEB home page).

Further alternatively, a small interfering polynucleotide molecule, according to the present invention can be a DNAzyme.

DNAzymes are single-stranded catalytic nucleic acid molecules. A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M Cuff Opin Mol Ther 2002; 4:119-21).

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 20002, Abstract 409, Ann Meeting Am Soc Gen Ther www(dot)asgt(dot)org). In another application, DNAzymes complementary to bcr-abl oncogenes were successful in inhibiting the oncogenes expression in leukemia cells, and lessening relapse rates in autologous bone marrow transplant in cases of CML and ALL.

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art.

Further according to embodiments of the present invention there is provided a use of the peptides as described herein in the manufacture of a medicament for treating a biological condition associated with GSK-3 activity, as described herein.

Further according to embodiments of the present invention there is provided a peptide as described herein, which is identified for use in the treatment of a biological condition associated with GSK-3 activity, as described herein.

In any of the methods and uses described herein, the peptides described herein can be utilized in combination with one or more additional active ingredient(s) or agent(s) which is capable of altering an activity of GSK-3, as described herein.

In any of the methods and uses described herein the peptide described herein can be utilized either per se, or, preferably, the peptide forms a part of a pharmaceutical composition, which may further comprise a pharmaceutically acceptable carrier.

As used herein a "pharmaceutical composition" refers to a preparation of one or more of the peptides described herein (as active ingredient), or physiologically acceptable salts or prodrugs thereof, with other chemical components including but not limited to physiologically suitable carriers, excipients, lubricants, buffering agents, antibacterial agents, bulking agents (e.g. mannitol), antioxidants (e.g., ascorbic acid or sodium bisulfite), anti-inflammatory agents, anti-viral agents, chemotherapeutic agents, anti-histamines and the like. The purpose of a pharmaceutical composition is to facilitate administration of a compound to a subject.

The term "active ingredient", which is also referred to herein interchangeably as "active agent" refers to a compound, which is accountable for a biological effect.

The terms "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, nasally, by inhalation, or parenterally, for example by intravenous drip or intraperitoneal, subcutaneous, intramuscular or intravenous injection, or topically (including opthalmically, vaginally, rectally and intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

In some embodiments, there is provided a pharmaceutical composition, as described herein, being formulated for nasal administration, as defined herein.

The amount of a composition to be administered will, of course, be dependent on the subject being treated, the severity of the affliction, the manner of administration, the judgment of the prescribing physician, etc.

The pharmaceutical composition may further comprise additional pharmaceutically active or inactive agents such as, but not limited to, an antibacterial agent, an antioxidant, a buffering agent, a bulking agent, a surfactant, an anti-inflammatory agent, an anti-viral agent, a chemotherapeutic agent and an anti-histamine.

According to an embodiment of the present invention, the pharmaceutical composition described herein is packaged in a packaging material and identified in print, in or on the packaging material, for use in the treatment of a medical condition associated with GSK-3 activity, as described herein.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

In some embodiments, the pharmaceutical composition is identified for use in combination with an additional active agent, as described herein.

In some embodiments, the pharmaceutical composition further comprises an additional active agent as described herein, being co-formulated with the peptide as described herein.

Further according to embodiments of the present invention there is provided a use of any of the peptides and/or the GSK-3 substrate competitive inhibitors as described herein in the manufacture of a medicament for treating a biological condition associated with GSK-3 activity, as described herein.

Further according to embodiments of the present invention there is provided a method of treating a biological condition associated with GSK-3 activity, as described herein, an/or of inhibiting a GSK-3 activity, which is effected by administering to a subject in need thereof any of the GSK-3 substrate competitive inhibitors as described herein.

Further according to embodiments of the present invention there is provided a GSK-3 substrate competitive inhibitor and/or a peptide as described herein, which is identified for use in the treatment of a biological condition associated with GSK-3 activity, as described herein.

In any of the methods and uses described herein the GSK-3 substrate competitive inhibitors as described herein can be utilized either per se, or, preferably, or forms a part of a pharmaceutical composition, which may further comprise a pharmaceutically acceptable carrier, as described herein.

General:

The terms "comprises", "comprising", "includes", "including", "having" and their conjugates mean "including but not limited to".

The term "consisting of" means "including and limited to".

The term "consisting essentially of" means that the composition, method or to structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the terms "polypeptide" and "peptide" encompass an amino acid sequence of any length including full-length proteins or portions thereof, wherein the amino acid residues are linked by covalent peptide bonds. Generally, an amino acid sequence of 50 amino acids and more are referred to herein as "polypeptide" or "protein", and an amino acid sequence of less than 50 amino acids is referred to herein as "peptide".

The term "peptide" as used herein encompasses also peptoids and semipeptoids which are peptide analogs, which may have, for example, modifications rendering the peptides more stable while in a body or more capable of penetrating into cells. Such modifications include, but are not limited to N-terminus modification, C-terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In some embodiments, the peptides described herein are chemically synthesized peptides.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom.

These modifications can occur at any of the bonds along the peptide chain and even at several (2-3) at the same time.

As used herein, the phrase "amino acid residue", which is also referred to herein, interchangeably, as "amino acid", describes an amino acid unit within a polypeptide chain. The amino acid residues within the peptides described herein can be either natural (naturally-occurring) or modified (non-naturally occurring) amino acid residues, as these phrases are defined hereinafter.

As used herein, the phrase "natural amino acid residue" describes an amino acid residue, as this term is defined hereinabove, which includes one of the twenty amino acids found in nature.

As used herein, the phrase "modified amino acid residue" describes an amino acid residue, as this term is defined hereinabove, which includes a natural amino acid that was subjected to a modification at its side chain. Such modifications are well known in the art and include, for example, incorporation of a functionality group such as, but not limited to, a hydroxy group, an amino group, a carboxy group and a phosphate group within the side chain. This phrase therefore includes, unless otherwise specifically indicated, chemically modified amino acids, including amino acid analogs (such as penicillamine, 3-mercapto-D-valine), naturally-occurring non-proteogenic amino acids (such as norleucine), and chemically-synthesized compounds that have properties known in the art to be characteristic of an amino acid. The term "proteogenic" indicates that the amino acid can be incorporated into a protein in a cell through well-known metabolic pathways.

Accordingly, as used herein, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids which are linked via a peptide bond or a peptide bond analog to at least one addition amino acid as this term is defined herein.

The peptides of the present embodiments are preferably utilized in a linear form, although it will be appreciated that in cases where cyclization does not severely interfere with peptide characteristics, cyclic forms of the peptide can also be utilized).

Cyclic peptides can either be synthesized in a cyclic form or configured so as to assume a cyclic form under desired conditions (e.g., physiological conditions).

The peptides of the present embodiments are preferably peptidomimetics, as this term is define hereinabove, which mimic the structural features of the critical amino acid motif $SX_1X_2X_3S(p)$, as is further detailed hereinabove.

Protein phosphorylation plays a crucial part in the biochemical control of cellular activity. Phosphorylation usually means formation of a phosphate ester bond between a phosphate ($PO_4$) group and an amino acid containing a hydroxyl (OH) group (tyrosine, serine and threonine). Many phosphorylation sites in proteins act as recognition elements for binding to other proteins, and those binding events activate or deactivate signaling and other pathways. Protein phosphorylation thus acts as a switch to turn biochemical signaling on and off.

The peptides according to the present embodiments can further include salts and chemical derivatives of the peptides. As used herein, the phrase "chemical derivative" describes a peptide as described herein having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. Also included as chemical derivatives are those peptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. The chemical derivatization does not comprehend changes in functional groups which change one amino acid to another.

As is mentioned hereinabove, some useful modifications are designed to increase the stability of the peptide in solution and, therefore, serve to prolong the half-life of the peptide in solutions, particularly biological fluids, such as blood, plasma or serum, by blocking proteolytic activity in the blood. Hence, the peptides described herein can have a stabilizing group at one or both termini. Typical stabilizing groups include amido, acetyl, benzyl, phenyl, tosyl, alkoxycarbonyl, alkyl carbonyl, benzyloxycarbonyl and the like end group modifications. Additional modifications include using one or more "D" amino acids in place of "L" amino acid(s), cyclization of the peptide inhibitor, and amide rather than amino or carboxy termini to inhibit exopeptidase activity.

The peptides described herein may or may not be glycosylated. The peptides are not glycosylated, for example, when produced directly by peptide synthesis techniques or are produced in a prokaryotic cell transformed with a recombinant polynucleotide. Eukaryotically-produced peptide molecules are typically glycosylated.

The term "hydrocarbon", as used herein, encompasses any moiety that is based on a linear and/or cyclic chain of carbons which are mainly substituted by hydrogens. A hydrocarbon can be a saturated or unsaturated moiety, and can optionally be substituted by one or more substituents, as described herein.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 2 to 10 carbon atoms. Most preferably, unless otherwise indicated, the alkyl is a lower alkyl having 2 to 6 carbon atoms. The alkyl group may be substituted or unsubstituted, as defined herein.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Representative examples are piperidine, piperazine, tetrahydrofurane, tetrahydropyrane, morpholino and the like.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted.

Whenever an alkyl, cycloalkyl, heteroalicyclic, aryl, heteroaryl or a hydrocarbon is substituted by one or more substituents, each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

A "hydroxy" group refers to an —OH group.

An "azide" group refers to a —N=N$^+$=N$^-$ group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R' group, where R' is defined as hereinabove.

A "thiocarbonyl" group refers to a —C(=S)—R' group, where R' is as defined herein.

A "C-carboxy" group refers to a —C(=O)—O—R' groups, where R' is as defined herein.

An "O-carboxy" group refers to an R'C(=O)—O— group, where R' is as defined herein.

An "oxo" group refers to a =O group.

A "carboxylate" or "carboxyl" encompasses both C-carboxy and O-carboxy groups, as defined herein.

A "carboxylic acid" group refers to a C-carboxy group in which R' is hydrogen. A "thiocarboxy" or "thiocarboxylate" group refers to both —C(=S)—O—R' and —O—C(=S)R' groups.

An "ester" refers to a C-carboxy group wherein R' is not hydrogen.

An ester bond refers to a —O—C(=O)— bond.

A "halo" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfonate" group refers to an —S(=O)$_2$—O—R' group, where R' is as defined herein.

A "sulfate" group refers to an —O—S(=O)$_2$—O—R' group, where R' is as defined as herein.

A "sulfonamide" or "sulfonamido" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR" group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

A "carbamyl" or "carbamate" group encompasses O-carbamyl and N-carbamyl groups.

A carbamate bond describes a —O—C(=O)—NR'— bond, where R' is as described herein.

An "O-thiocarbamyl" group refers to an —OC(=S)—NR'R" group, where each of R' and R" is as defined herein.

An "N-thiocarbamyl" group refers to an R'OC(=S) NR"— group, where each of R' and R" is as defined herein.

A "thiocarbamyl" or "thiocarbamate" group encompasses O-thiocarbamyl and N-thiocarbamyl groups.

A thiocarbamate bond describes a —O—C(=S)—NR'— bond, where R' is as described herein.

A "C-amido" group refers to a —C(=O)—NR'R" group, where each of R' and R" is as defined herein.

An "N-amido" group refers to an R'C(=O)—NR"— group, where each of R' and R" is as defined herein.

An "amide" group encompasses both C-amido and N-amido groups.

An amide bond describes a —NR'—C(=O)— bond, where R' is as defined herein.

A "urea" group refers to an —N(R')—C(=O)—NR"R'" group, where each of R' and R" is as defined herein, and R'" is defined as R' and R" are defined herein.

A "nitro" group refers to an —NO$_2$ group.

A "cyano" group refers to a —C≡N group.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

A "phosphoric acid" is a phosphate group is which each of R is hydrogen.

The term "phosphinyl" describes a —PR'R" group, with each of R' and R" as defined hereinabove.

The term "thiourea" describes a —N(R')—C(=S)—NR"— group, with each of R' and R" as defined hereinabove.

Any of the substances described herein (e.g., peptides, polypeptides or small molecules), can be in a form of a pharmaceutically acceptable salt thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound.

The present invention further encompasses prodrugs, solvates and hydrates of the substances described herein.

As used herein, the term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. The prodrug may also have improved solubility as compared with the parent drug in pharmaceutical compositions. Prodrugs are also often used to achieve a sustained release of the active compound in vivo. An example, without limitation, of a prodrug would be a peptide, as described herein, having one or more carboxylic acid moieties, which is administered as an ester (the "prodrug"). Such a prodrug is hydrolysed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the peptide) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Material and Methods

Materials:

Bacterially expressed Purified GSK-3β Wild-Type (WT) was prepared as previously described (Eldar-Finkelman 1996 PNAS).

Peptide inhibitors L803 KEAPPAPPQS(p)P (SEQ ID NO:4) and L803-mts (SEQ ID NO:43) in which myristic acid was attached via a Gly residue to its N-terminus were described previously [Plotkin et al., 2003, supra].

Other peptides are described hereinbelow.

Radioactive materials were purchased from NEN PerkinElmer USA.

GSK-3β F93A mutant (in which Phe93 was replaced by alanine) was prepared as described in WO 2012/101599.

In Vitro Kinase Assays:

GSK-3β (WT) was incubated with pIRS-1, RREGGMSRPAS(p)VDG (SEQ ID NO:55), as an exemplary substrate, in a reaction mixture (50 mM Tris-HCl, pH 7.3, 10 mM magnesium acetate, and 0.01% β-mercaptoethanol) together with 100 μM 32P[γ-ATP] (0.5 μCi/assay) for 15 minutes. Reactions were stopped by spotting on p81 paper (Whatman), washed with phosphoric acid, and counted for radioactivity as previously described [Ilouz et al. (2006) supra].

In assays conducted with GSK-3 mutant, the GSK-3β proteins (WT or mutant) were incubated with the indicated substrate in a reaction mixture (50 mM Tris-HCl, pH 7.3, 10 mM magnesium acetate, and 0.01% β-mercaptoethanol) together with 100 μM $^{32}$P[γ-ATP] (0.5 μCi/assay) for 15 minutes. Reactions were stopped by spotting on p81 paper (Whatman) washed with phosphoric acid, and counted for radioactivity as previously described [Ilouz et al. (2006) supra]. In assays from cells overexpressing GSK-3 proteins, GSK-3 proteins were partially purified by DE-52 minicolumn and subjected to in vitro kinase assays as described. The activity of the endogenous GSK-3 that was determined in cells transfected with the pCMV4 vector was subtracted from the activity values obtained for WT and mutants.

Statistical Analysis:

Data were analyzed with Origin Professional 6.0 software using Student's t-test to compare GSK-3 activity for peptides-treatment vs. non treatment. Data were considered significant at $p<0.05$.

Molecular Modeling:

The computational determination of the binding modes of the different peptides to GSK-3 generally followed the procedure described in Licht-Murava, et al. 2011, supra). It consisted of a molecular dynamics (MD) simulation of the free peptide in water, rigid body docking of selected conformers of the free peptide to GSK-3 and refinement via MD of selected docking models.

The structure of HSF-1 is not available and therefore helical initial models of pHSF-1 and its mutants were constructed; this choice was based on the structures of pCREB (Radhakrishnan et al., Cell 91(6): 741-752, 1997) and its predicted complex with GSK-3 (Ilouz et al. 2006, supra). Also, poly-proline and proline rich sequences tend to form helical structures.

In every case the initial model was immersed in a cube of water, the system was neutralized and energy minimized, providing a starting structure for MD simulation. The simulation consisted of two steps: (1) water equilibration (100 ps), keeping the non-hydrogen atoms of the peptide restrained and allowing movement of the hydrogen atoms and the solvent molecules; and (2) MD of the solvated peptide (10 ns), allowing free movement for all the atoms in the system.

The root mean square deviation (RMSD) between frames along the MD trajectory and the starting structure was used to assess the peptide's structure stabilization. All non-hydrogen atoms of the peptide were used in these RMSD calculations, which therefore reflected both, back-bone and side-chain mobility.

Clustering was performed for the last 7-8 ns of the trajectory, after stabilization was achieved, using cutoff value of 1.1 Å, selected so that the final number of clusters did not exceed 10. As in the RMSD calculations, all non-hydrogen atoms of the peptide were considered in the clustering.

The central structures from the MD clusters were used in the docking step. The energy minimizations and MD simulations were performed with Gromacs [Van Der Spoel et al. (2005) *J. Comput. Chem.* 26, 1701-18], employing the united atoms gromos96 43a1 force field (Lindahl et al., Journal of Molecular Modeling 7(8): 306-317, 2001) augmented with parameterization for phosphorylated residues [www(dot)gromacs(dot)org/Downloads/User_contributions/Force_fields]. The Gromacs package utilities g_rms and g_cluster were used for RMSD calculations and clustering of the trajectory.

Rigid body docking was performed with the geometric-electrostatic-hydrophobic version of MolFit Berchanski et al. (2004) *Proteins* 351, 309-26]. Standard translation and rotation intervals of 1.05 Å and 12°, respectively, were employed, as previously described [Kowalsman & Eisenstein (2009) *Proteins* 77, 297-318]. In these docking computations, a model structure of GSK-3 with phosphorylated Y216, as previously described [Ilouz et al; 2006, supra] was used. The exhaustive rotation/translation searches with MolFit were followed with a post-scan filtering procedure, which was based on the statistical and solvation properties of the predicted interfaces (Kowalsman and Eisenstein 2009, supra). The filtered models were further screened requesting that the phosphate oxygens of the pre-phosphorylated serine of the peptide make at least ten contacts of 5 Å or less with the side-chain ends of residues R96, R180 and K205, which define the positive phosphate binding pocket of GSK-3. These models are referred to as acceptable models.

The acceptable models underwent rigid body optimization of the relative orientation of the molecules with MolFit, using stepwise rotations of 2° about the principal axes. They were further subjected to energy minimization and MD simulation with Gromacs of the ternary complexes—GSK-3, ATP-$Mg^{2+}$ and the relevant peptide, all immersed in water and neutralized. Each simulation consisted of 3 steps: (1) solvent equilibration (200 ps), in which only the solvent and the hydrogen atoms of the complex were not restrained; (2) peptide equilibration (200 ps), in which the peptide was free to move together with the solvent; (3) structure equilibration (2 ns), in which only the Cα atoms of GSK-3 were restrained. Models in which the phosphorylated serine of the peptide moved significantly away from the phosphate binding pocket of GSK-3 during the simulation were discarded.

UCSF-Chimera software (Sanner, Olson et al. 1996, Pettersen, Goddard et al. 2004) was used for visualization of the results; comparison between different models, and preparation of the figures.

Comparisons between different peptides were based on RMSDs calculated for the back bone plus Cβ atoms; a variable referred to herein as RMSD-Cβ.

Example 1

Novel Selective GSK-3 Peptide Inhibitors

The GSK-3 substrate HSF-1 KEEPPSPPQS(p)P (SEQ ID NO:3) features the recognition motif of GSK-3 as described herein, and further features Glu residue at the third position upstream the serine residue. L803 (SEQ ID NO:4), a known inhibitor of GSK-3, features an alanine residue instead of the serine residue, and an alanine residue instead of the Glu residue at the third position upstream the serine residue.

An exemplary novel peptide has now been synthesized, after the HSF-1 substrate, in which only the Glu residue at the third position upstream the serine residue is replaced by an alanine residue, whereby the serine residue at the third position upstream the phosphorylated serine residue is maintained. This peptide is termed herein L807 and is represented by the following amino acid sequence:

(SEQ ID NO: 9)
KEAPPSPPQS(p)P

Another exemplary novel peptide has been synthesized, in which myristic acid was attached via a Gly residue to the N-terminus of L807. This peptide is termed L807-mts, and is represented by the following amino acid sequence:

(SEQ ID NO: 10)
myristic acid-GKEAPPSPPQS(p)P

Example 2

Activity Assays

The ability of the novel peptides described in Example 1 to inhibit GSK-3β was determined by in vitro kinase assays as described hereinabove. The results are presented in FIGS. 2A-B. Substrate phosphorylation obtained in reaction with no inhibitor was defined as 100% (Con), and the results presented are means of two independent experiments each performed in duplicate±SEM.

FIG. 2A shows the inhibition of GSK-3 by L807 or L803 in in vitro kinase assays. FIG. 2B shows the inhibition of GSK-3 by L807-mts and L803-mts in in vitro kinase assays. The superior inhibition activity of L807 as compared to both L803 and L803-mts is clearly demonstrated. The superior inhibition activity of L807-mts as compared to both L803 and L803-mts is also clearly demonstrated.

As can be seen in FIGS. 2A-B, $IC_{50}$ of L807 is 16 µM whereby of L803 it is 200 µM. Similarly $IC_{50}$ of L807-mts is 0.24 µM whereby that of L803-mts is 40 µM.

Further studies were conducted in order to determine whether L807 is a substrate of GSK-3. Thus, in vitro kinase assays as described hereinabove were performed in the presence of pIRS-1 substrate or L807 and phosphorylation was determined.

FIG. 3 presents the obtained results and shows that L807 is a substrate of GSK-3.

Additionally, the effect of double phosphorylation of the peptide was tested. To this effect a double phosphorylated peptide in which the serine residue of L807 was phosphorylated was prepared by subjecting L807 to phosphorylation by GSK-3 in 'cold' assay conditions, as described hereinabove. In vitro kinase assays were performed as described hereinabove except that 0.5M ATP was included in the reaction to confirm maximal phosphorylation.

The obtained double phosphorylated peptide is termed herein pL807 and has the following amino acid sequence:

(SEQ ID NO: 44)
KEAPPS(p)PPQS(p)P

As can further be seen in FIG. 3, pL807 is not a substrate of GSK-3.

In vitro kinase assays performed with pIRS-1 as substrate and pL807 it was shown that pL807 also does not inhibit GSK-3, as can be seen in FIG. 4.

It may be deduced from the above-described assays that L807 is converted into an inhibitor of GSK-3 upon its phosphorylation within the catalytic cavity of GSK-3. That is, after its binding to GSK-3, L807 is phosphorylated, and thereby converted into pL807 while ATP is converted to ADP. The formed pL807 then undergoes conformational changes that strengthen its binding to GSK-3 and thus produces the inhibitory effect. When pL807 is used, it cannot bind to GSK-3, presumably since GSK-3 remains bound to ATP, and the latter prevents the pL807 binding. In the case of L807, it is assumed that since it interacts with ATP, and is thereby phosphorylated, it can bind GSK-3.

In order to further explore the binding of L807 and pL807 to the catalytic binding site of GSK-3, assays were conducted while using the GSK-3β mutant F93A.

Thus, L807 and the substrate pHSF-1 were both tested in in vitro kinase assays as described hereinabove, for the ability of GSK-3β (WT) and its F93A mutant to phosphorylate these peptides.

The results are presented in FIG. 5, and show the level of phosphorylation of pHSF-1 and L807, when used as substrates, by wild-type (WT) GSK-3 or F93A mutant. As can be seen, L807 is phosphorylated by both GSK-3 and F93A. These results indicate that L807 does not interact with F93.

As can further be seen in FIG. 5, similar results were obtained for pHSF-1. It is noted that these results are different from other GSK-3 substrates (pGS-1, pIRS-1 and p9CREB) that were not phosphorylated by the F93A mutant (see, Licht-Murava et al. 2011, supra). Evidently the binding of pHSF-1 to GSK-3 differs from that of other peptidic substrates and from that of the inhibitor L803, which was derived from pHSF-1.

In vitro kinase assays conducted for evaluating the inhibition activity of L807 and pL807 of the F93A mutant were also conducted, using pIRS-1 as a substrate.

The results are presented in FIG. 6 and show that inhibition of GSK-3 by L807 requires interaction with Phe93, since no inhibition was observed by L807 for the F93A mutant.

Example 3

Computational Modeling

In parallel to the experimental studies computational docking of L807 and pL807 to GSK-3/ATP was performed in order to better understand the structural aspect of the interaction. The obtained images are presented in FIG. 7, with L807 shown in purple, pL807 shown in yellow, the solvent accesible surface of GSK-3 is shown in gray, the positive cavity in blue, the P-loop in green, the substrate binding pocket (Q89, F93 and N95) in orange and the hydrophobic surface (V214, Y216 and I217) in beige. The binding mode of pL807 was obtained via molecular dynamics simulation. The model-structure of a GSK-3/ATP/L807 complex was modified by replacing ATP with ADP and S6 of L807 was replaced with S6p, producing a starting structure of GSK-3/ADP/pL807. The simulation showed that the conformation and binding mode change of pL807 occur without dissociation from GSK-3/ADP.

The computational docking of L807 is shown in the top panel, of pL807 in the central panel) and of both L807 and pL807 in the bottom panel, predicting the binding mode of the peptides to GSK-3. The computational docking is in agreement with the experimental results, as it shows that L807 is likely a substrate (FIG. 7, top panel). Preliminary results for the docking of pL807 to GSK-3/ADP (FIG. 7, central panel) suggest that the peptide changes conformation upon phosphorylation and shifts into the active site so that the newly phosphorylated S6 replaces the pre-phosphorylated S10(p) and interacts with the positive cavity of GSK-3.

Importantly, and further in agreement with the experimental data, L807 does not interact with F93 (Phe93), whereby a strong interaction is observed for pL807, as a result of the conformational changes.

For comparison, A computational model of the ternary complex between GSK-3, ATP-$Mg^{2+}$ and pHSF-1 was constructed as described in the Methods section.

The molecular dynamics (MD) simulation of free pHSF-1 in water showed stabilization of the peptide structure after approximately 1.5 ns. A RMSD deviation of ±1 Å from the average was obtained for the remaining part of the trajectory. Clustering of the last 8 ns of the trajectory produced 7 clusters, with average RMSD of 2.81±0.75 Å between their central conformers.

Each of the central conformers, representing the clusters, was docked to GSK-3, employing a full rotational-translational search followed by filtering based on statistical and solvation properties of the predicted interfaces.

The predicted binding mode of GSK-3 with pHSF-1 suggests that pHSF-1 peptide makes contact with the positive phosphate binding pocket of GSK-3 and with the P-loop; its S6 Oγ points at the γ phosphate of ATP and is hydrogen-bonded to the side chain of GSK-3 5203.

After about 1 ns of the simulation the peptide shifted to a slightly different location and maintained this pose for the rest of the simulation. Most of the contacts with GSK-3 were retained, but atom S6 Cβ moved to 9.6 Å away from the ATP Pγ atom, which may be indicative for a dissociating peptide.

The computational docking models of pHSF-1 agree well with the experimental mutation data, which show that the binding of this substrate and its phosphorylation do not depend on GSK-3 residues F93 or V214. The binding of pHSF-1 appears to be stabilized by charged interactions within the GSK-3 positive binding pocket and contacts with the P-loop. The latter contacts help to orient the peptide within the GSK-3 substrate binding trough, located between its N- and C-terminal lobes. This mode of binding is adequate for a substrate, as it positions the phosphorylation target residue near the reaction center. It however does not involve many hydrophobic contacts, allowing fast dissociation when the phosphorylation reaction is completed.

The binding mode of pHSF-1 is considerably different from that of L803, whose binding is driven by hydrophobic interactions, as previously reported. Thus, L803 interacts with the positive cavity of GSK-3 through residue $S10_p$ but it does not interact with the P-loop. Instead, L803 contacts GSK-3 residue F93 and the hydrophobic surface patch formed by residues V214, Y216 and I217 (Licht-Murava, et al. 2011, supra).

Example 4

In Vivo Studies

Animals and Behavior Tests:

5XFAD mice were purchased from Jackson laboratory and maintained at an animal house. The 5XFAD mice were randomly assigned to two groups (6 animals each). Treatment started at the age of 2 months, by administering, intranassally, L807-mts (60 μg) (5 μl solution in each nostril) every other day for 120 days.

A contextual fear conditioning test (FCT) was thereafter conducted as described in Saura et al. (2005) J. Neurosci. 25(29), 6755-6764. Briefly, mice were subjected to an unconditioned electric stimulus (US footshock; 1 s/1 mA) in a training pre-session. Twenty-four hours later, FCT was measured by scoring freezing behavior (the absence of all but respiratory movement) for 180 seconds using a FreezeFrame automated scoring system (Coulbourn Instruments). All experiments were in compliance with protocols approved by the TAU animal care committee.

Histology and Aβ Staining:

Saline-perfused brains of the tested mice were rapidly excised and frozen in $N_2$. Brains were divided into the two hemispheres: the left hemisphere was taken for immunohistology and the right hemisphere for immunoblot analysis. Coronal brains sections (14 μm) were cut by cryostat at −20° C. Slices at Bregma −1.58 mm were fixed (using 4% PFA) and stained with Congo red dye (Sigma-Aldrich) or with an antigen-retrieval method with anti-Aβ 6E10 antibody (SIG-39300) and visualized by fluorescence microscopy. Quantification of Aβ depositions was done for the whole hippocampus area in a blinded fashion using Imaging Research software from the NIH in an unbiased stereological approach.

Results:

The '5XFAD' mouse model was used to determine the in vivo therapeutic effect of L807-mts, as an exemplary GSK-3 inhibitor according to some embodiments of the present invention. 5XFAD mice co-express a total of five familial Alzheimer's disease (AD) mutations in APP and presenilin-1 (PS1) and develop massive cerebral Aβ loads, cognitive decline, and neuronal loss [See, for example, Oakley et al. (2006) *J. Neurosci.* 26(40), 10129-10140]. These mice serve as a suitable mouse model for AD.

Mice (two-month old) were treated intranasally with L807-mts (60 μg/dose) for 120 days. At the end of the experiment mice were subjected to the contextual fear conditioning test (FCT), a behavioral test widely used to evaluate associative learning and memory (see, Saura et al. (2005) supra).

Scoring freezing behavior indicated that treatment with L807-mts improved performance by up to 81%±14% of wild-type (WT) mice (FIG. 8A).

Mice were scarified and coronal brain sections were stained with congo red dye and Aβ loads were visualized by fluorescence microscopy. The obtained images, presented in FIG. 8B, clearly show that the amount and the mean sizes of AO loads were largely reduced in the L807-mts treated mice.

Example 5

Comparative Kinetic Studies

Comparative studies are conducted in order to determine the kinetics of the interaction of L807 and pL807 peptides described herein with GSK-3β.

In vitro kinase assays are performed as described hereinabove and Km values are determined therefrom for reactions performed in the presence of L807 (or L807-mts), pL807 (or pL807-mts) and exemplary GSK-3 substrates (e.g., pHSF-1 or pIRS-1), each alone, and then for studies conducted with a combination of L807 or pL807 and the GSK-3 substrate, and of the two GSK-3 substrates.

These assays show that the Km value in the presence of a GSK-3 substrate remains substantially unchanged when tested in the presence of another GSK-3 substrate, yet, is substantially increased when tested in the presence of L807 (or L807-mts).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A peptide having the amino acid sequence II:

$$[Yn\text{---}Y_3Y_2Y_1]ZX_1X_2X_3Z(p)[W_1\text{---}Wm] \quad \text{(II)}$$

wherein:

n is 5, 6 or 7, m is 1, 2, 3, 4 or 5;

m and n are such that the peptide consists of no more than 15 amino acid residues;

Z(p) is a phosphorylated serine residue or a phosphorylated threonine residue;

Z is a serine residue or a threonine residue;

$X_1$, $X_2$, $X_3$ and $W_1$-Wm are each independently any amino acid residue; and $Y_1$-Yn comprises an amino acid sequence as set forth in SEQ ID NO:8:

Lys-Glu-$Y_3$-Pro-Pro    (SEQ ID NO: 8)

wherein $Y_3$ is any amino acid residue excepting a glutamic acid residue.

2. The peptide of claim 1, wherein $Y_3$ is an amino acid residue having a Log P higher than −3.

3. The peptide of claim 1, wherein $Y_3$ is an alanine residue.

4. The peptide of claim 1, wherein at least one of $X_1$, $X_2$, $X_3$ and $W_1$-Wm is identical to a corresponding amino acid sequence of HSF-1.

5. The peptide of claim 1, wherein Z is a serine residue.

6. The peptide of claim 1, wherein Z(p) is a phosphorylated serine residue.

7. The peptide of claim 1, having an amino acid sequence as set forth in SEQ ID NO:9.

8. The peptide of claim 1, further comprising a hydrophobic moiety attached thereto.

9. The peptide of claim 8, having the amino acid sequence as set forth in SEQ ID NO:10.

10. A pharmaceutical composition comprising, as an active ingredient, the peptide of claim 1, and a pharmaceutically acceptable carrier.

11. A pharmaceutical composition comprising, as an active ingredient, a peptide, being of no more than 15 amino acid residues, and having an amino acid sequence which comprises a $ZX_1X_2X_3Z(p)$ recognition motif of a native GSK-3 substrate, wherein Z(p) is a phosphorylated serine residue or a phosphorylated threonine residue; Z is a serine residue or a threonine residue, and each of $X_1$, $X_2$ and $X_3$ is any amino acid, the peptide having an amino acid sequence upstream said Z in which at least one polar or charged amino acid residue in an amino acid sequence upstream said serine or threonine residue of said native GSK-3 substrate is replaced by at least one amino acid residue selected from the group consisting of a non-polar amino acid residue, a non-charged amino acid residue (at a physiological pH) and a hydrophobic amino acid residue, the peptide exhibiting an inhibition activity towards GSK-3, such that when a GSK-3 reacts with a GSK-3 substrate in the presence of the peptide, an apparent Michaelis Constant (app Km value) of the GSK-3 substrate is higher than a Michaelis Constant (Km value) obtained in a similar assay in the absence of the peptide inhibitor, and a pharmaceutically acceptable carrier.

12. A method of inhibiting an activity of GSK-3, the method comprising contacting cells expressing GSK-3 with an effective amount of the peptide of claim 1.

13. A method of inhibiting an activity of GSK-3, the method comprising contacting cells expressing GSK-3 with an effective amount of a peptide, being of no more than 15 amino acid residues, and having an amino acid sequence which comprises a $ZX_1X_2X_3Z(p)$ recognition motif of a native GSK-3 substrate, wherein $Z(p)$ is a phosphorylated serine residue or a phosphorylated threonine residue; Z is a serine residue or a threonine residue, and each of $X_1$, $X_2$ and $X_3$ is any amino acid, the peptide having an amino acid sequence upstream said Z in which at least one polar or charged amino acid residue in an amino acid sequence upstream said serine or threonine residue of said native GSK-3 substrate is replaced by at least one amino acid residue selected from the group consisting of a non-polar amino acid residue, a non-charged amino acid residue (at a physiological pH) and a hydrophobic amino acid residue, the peptide exhibiting an inhibition activity towards GSK-3, such that when a GSK-3 reacts with a GSK-3 substrate in the presence of the peptide, an apparent Michaelis Constant (app Km value) of the GSK-3 substrate is higher than a Michaelis Constant (Km value) obtained in a similar assay in the absence of the peptide inhibitor.

14. A method of treating a biological condition associated with GSK-3 activity, the method comprising administering to a subject in need thereof a therapeutically effective amount of the peptide of claim 1.

15. A method of treating a biological condition associated with GSK-3 activity, the method comprising administering to a subject in need thereof a therapeutically effective amount of a peptide, being of no more than 15 amino acid residues, and having an amino acid sequence which comprises a $ZX_1X_2X_3Z(p)$ recognition motif of a native GSK-3 substrate, wherein $Z(p)$ is a phosphorylated serine residue or a phosphorylated threonine residue; Z is a serine residue or a threonine residue, and each of $X_1$, $X_2$ and $X_3$ is any amino acid, the peptide having an amino acid sequence upstream said Z in which at least one polar or charged amino acid residue in an amino acid sequence upstream said serine or threonine residue of said native GSK-3 substrate is replaced by at least one amino acid residue selected from the group consisting of a non-polar amino acid residue, a non-charged amino acid residue (at a physiological pH) and a hydrophobic amino acid residue, the peptide exhibiting an inhibition activity towards GSK-3, such that when a GSK-3 reacts with a GSK-3 substrate in the presence of the peptide, an apparent Michaelis Constant (app Km value) of the GSK-3 substrate is higher than a Michaelis Constant (Km value) obtained in a similar assay in the absence of the peptide inhibitor.

16. A peptide having the amino acid sequence II*:

$$[Yn\cdots Y_3Y_2Y_1]Z(p)_1X_2X_3Z(p)_2[W_1\cdots Wm] \qquad (II^*)$$

wherein:

n is 5, 6 or 7, m is 1, 2, 3, 4 or 5;

m and n are such that the peptide consists of no more than 15 amino acid residues;

$Z(p)_1$ and $Z(p)_2$ are each independently a phosphorylated serine residue or a phosphorylated threonine residue;

$X_1$, $X_2$, $X_3$ and $W_1$-Wm are each independently any amino acid residue; and $Y_1$-Yn comprises an amino acid sequence as set forth in SEQ ID NO:8:

(SEQ ID NO: 8)
Lys-Glu-$Y_3$-Pro-Pro wherein $Y_3$ is any amino acid residue excepting a glutamic acid residue.

17. The composition of claim 11, wherein said at least one amino acid sequence upstream said Z is such that when said Z is phosphorylated upon interaction with the catalytic binding site of GSK-3, a phosphorylated peptide obtained by said interaction exhibits a dissociation constant lower than a dissociation constant of said native GSK-3 substrate by at least 2-folds.

18. The composition of claim 11, wherein said amino acid residue upstream said Z is selected from the group consisting of alanine residue, glycine residue, valine residue, leucine residue, isoleucine residue, proline residue, methionine residue, cysteine residue, tryptophan residue, tyrosine residue and phenylalanine residue.

19. The composition of claim 11, having an amino acid sequence I:

$$[Yn\cdots Y_3Y_2Y_1]ZX_1X_2X_3Z(p)[W_1\cdots Wm] \qquad (I)$$

wherein:

m equals 1, 2, 3, 4 or 5;

n is 3, 4, 5, 6 or 7, such that m and n are such that said peptide consists of no more than 15 amino acid residues;

$Z(p)$ is said phosphorylated serine residue or said phosphorylated threonine residue;

Z is said serine residue or said threonine residue;

$X_1$, $X_2$, $X_3$, $Y_1$-Yn and $W_1$-Wm are each independently an amino acid residue of said substrate, except that at least one charged or polar amino acid residue of said $Y_1$-Yn in said native GSK-3 substrate is replaced by said at least one amino acid residue selected from the group consisting of a non-polar amino acid residue, a non-charged amino acid residue (at a physiological pH) and a hydrophobic amino acid residue.

20. The composition of claim 11, wherein said peptide further comprises a hydrophobic moiety attached thereto.

21. The method of claim 13, wherein said at least one amino acid sequence upstream said Z is such that when said Z is phosphorylated upon interaction with the catalytic binding site of GSK-3, a phosphorylated peptide obtained by said interaction exhibits a dissociation constant lower than a dissociation constant of said native GSK-3 substrate by at least 2-folds.

22. The method of claim 13, wherein said amino acid residue upstream said Z is selected from the group consisting of alanine residue, glycine residue, valine residue, leucine residue, isoleucine residue, proline residue, methionine residue, cysteine residue, tryptophan residue, tyrosine residue and phenylalanine residue.

23. The method of claim 13, having an amino acid sequence I:

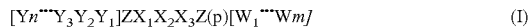
$$[Yn\cdots Y_3Y_2Y_1]ZX_1X_2X_3Z(p)[W_1\cdots Wm] \quad (I)$$

wherein:
m equals 1, 2, 3, 4 or 5;
n is 3, 4, 5, 6 or 7, such that m and n are such that said peptide consists of no more than 15 amino acid residues;
Z(p) is said phosphorylated serine residue or said phosphorylated threonine residue;
Z is said serine residue or said threonine residue;
$X_1$, $X_2$, $X_3$, $Y_1$-Yn and $W_1$-Wm are each independently an amino acid residue of said substrate, except that at least one charged or polar amino acid residue of said $Y_1$-Yn in said native GSK-3 substrate is replaced by said at least one amino acid residue selected from the group consisting of a non-polar amino acid residue, a non-charged amino acid residue (at a physiological pH) and a hydrophobic amino acid residue.

24. The method of claim 13, wherein said peptide further comprises a hydrophobic moiety attached thereto.

25. The method of claim 15, wherein said at least one amino acid sequence upstream said Z is such that when said Z is phosphorylated upon interaction with the catalytic binding site of GSK-3, a phosphorylated peptide obtained by said interaction exhibits a dissociation constant lower than a dissociation constant of said native GSK-3 substrate by at least 2-folds.

26. The method of claim 15, wherein said amino acid residue upstream said Z is selected from the group consisting of alanine residue, glycine residue, valine residue, leucine residue, isoleucine residue, proline residue, methionine residue, cysteine residue, tryptophan residue, tyrosine residue and phenylalanine residue.

27. The method of claim 15, having an amino acid sequence I:

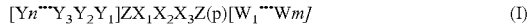
$$[Yn\cdots Y_3Y_2Y_1]ZX_1X_2X_3Z(p)[W_1\cdots Wm] \quad (I)$$

wherein:
m equals 1, 2, 3, 4 or 5;
n is 3, 4, 5, 6 or 7, such that m and n are such that said peptide consists of no more than 15 amino acid residues;
Z(p) is said phosphorylated serine residue or said phosphorylated threonine residue;
Z is said serine residue or said threonine residue;
$X_1$, $X_2$, $X_3$, $Y_1$-Yn and $W_1$-Wm are each independently an amino acid residue of said substrate, except that at least one charged or polar amino acid residue of said $Y_1$-Yn in said native GSK-3 substrate is replaced by said at least one amino acid residue selected from the group consisting of a non-polar amino acid residue, a non-charged amino acid residue (at a physiological pH) and a hydrophobic amino acid residue.

28. The method of claim 15, wherein said peptide further comprises a hydrophobic moiety attached thereto.

* * * * *

SEQUENCE LISTING

```
<160> NUMBER OF SEQ ID NOS: 55

<210> SEQ ID NO 1
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Serine or threonine residue
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Serine or threonine residue
<220> FEATURE:
<221> NAME/KEY: MOD_RES
<222> LOCATION: (5)..(5)
<223> OTHER INFORMATION: PHOSPHORYLATION

<400> SEQUENCE: 1

Xaa Xaa Xaa Xaa Xaa
1               5

<210> SEQ ID NO 2
<211> LENGTH: 7
<212> TYPE: PRT
<213> ORGANISM: Artificial sequence
<220> FEATURE:
<223> OTHER INFORMATION: 89-95 loop of GSK-3
```

-continued

<400> SEQUENCE: 2

Gln Asp Lys Arg Phe Lys Asn
1               5

<210> SEQ ID NO 3
<211> LENGTH: 11
<212> TYPE: PRT
<213> ORGANISM: Artificial sequence
<220> FEATURE:
<223> OTHER INFORMATION: Binding motif of the HSF-1 (pHSF-1)
<220> FEATURE:
<221> NAME/KEY: MOD_RES
<222> LOCATION: (10)..(10)
<223> OTHER INFORMATION: PHOSPHORYLATION

<400> SEQUENCE: 3

Lys Glu Glu Pro Pro Ser Pro Pro Gln Ser Pro
1               5                   10

<210> SEQ ID NO 4
<211> LENGTH: 11
<212> TYPE: PRT
<213> ORGANISM: Artificial sequence
<220> FEATURE:
<223> OTHER INFORMATION: Inhibitor L803
<220> FEATURE:
<221> NAME/KEY: MOD_RES
<222> LOCATION: (10)..(10)
<223> OTHER INFORMATION: PHOSPHORYLATION

<400> SEQUENCE: 4

Lys Glu Ala Pro Pro Ala Pro Pro Gln Ser Pro
1               5                   10

<210> SEQ ID NO 5
<211> LENGTH: 433
<212> TYPE: PRT
<213> ORGANISM: Homo sapiens

<400> SEQUENCE: 5

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
                20                  25                  30

Asp Gly Ser Lys Val Thr Thr Val Ala Thr Pro Gly Gln Gly Pro
            35                  40                  45

Asp Arg Pro Gln Glu Val Ser Tyr Thr Asp Thr Lys Val Ile Gly Asn
        50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly

```
                    165                 170                 175
Ile Cys His Arg Asp Ile Lys Pro Gln Asn Leu Leu Leu Asp Pro Asp
                180                 185                 190
Thr Ala Val Leu Lys Leu Cys Asp Phe Gly Ser Ala Lys Gln Leu Val
            195                 200                 205
Arg Gly Glu Pro Asn Val Ser Tyr Ile Cys Ser Arg Tyr Tyr Arg Ala
        210                 215                 220
Pro Glu Leu Ile Phe Gly Ala Thr Asp Tyr Thr Ser Ser Ile Asp Val
225                 230                 235                 240
Trp Ser Ala Gly Cys Val Leu Ala Glu Leu Leu Leu Gly Gln Pro Ile
                245                 250                 255
Phe Pro Gly Asp Ser Gly Val Asp Gln Leu Val Glu Ile Ile Lys Val
            260                 265                 270
Leu Gly Thr Pro Thr Arg Glu Gln Ile Arg Glu Met Asn Pro Asn Tyr
        275                 280                 285
Thr Glu Phe Lys Phe Pro Gln Ile Lys Ala His Pro Trp Thr Lys Asp
    290                 295                 300
Ser Ser Gly Thr Gly His Phe Thr Ser Gly Val Arg Val Phe Arg Pro
305                 310                 315                 320
Arg Thr Pro Pro Glu Ala Ile Ala Leu Cys Ser Arg Leu Leu Glu Tyr
                325                 330                 335
Thr Pro Thr Ala Arg Leu Thr Pro Leu Glu Ala Cys Ala His Ser Phe
            340                 345                 350
Phe Asp Glu Leu Arg Asp Pro Asn Val Lys Leu Pro Asn Gly Arg Asp
        355                 360                 365
Thr Pro Ala Leu Phe Asn Phe Thr Thr Gln Glu Leu Ser Ser Asn Pro
    370                 375                 380
Pro Leu Ala Thr Ile Leu Ile Pro Pro His Ala Arg Ile Gln Ala Ala
385                 390                 395                 400
Ala Ser Thr Pro Thr Asn Ala Thr Ala Ala Ser Asp Ala Asn Thr Gly
                405                 410                 415
Asp Arg Gly Gln Thr Asn Asn Ala Ala Ser Ala Ser Ala Ser Asn Ser
            420                 425                 430
Thr

<210> SEQ ID NO 6
<211> LENGTH: 433
<212> TYPE: PRT
<213> ORGANISM: Artificial sequence
<220> FEATURE:
<223> OTHER INFORMATION: GSK-3 beta, F93A mutant

<400> SEQUENCE: 6

Met Ser Gly Arg Pro Arg Thr Thr Ser Phe Ala Glu Ser Cys Lys Pro
1               5                   10                  15
Val Gln Gln Pro Ser Ala Phe Gly Ser Met Lys Val Ser Arg Asp Lys
                20                  25                  30
Asp Gly Ser Lys Val Thr Thr Val Val Ala Thr Pro Gly Gln Gly Pro
            35                  40                  45
Asp Arg Pro Gln Glu Val Ser Tyr Thr Asp Thr Lys Val Ile Gly Asn
        50                  55                  60
Gly Ser Phe Gly Val Val Tyr Gln Ala Lys Leu Cys Asp Ser Gly Glu
65                  70                  75                  80
Leu Val Ala Ile Lys Lys Val Leu Gln Asp Lys Arg Ala Lys Asn Arg
                85                  90                  95
```

```
Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365

Thr Pro Ala Leu Phe Asn Phe Thr Thr Gln Glu Leu Ser Ser Asn Pro
    370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
            420                 425                 430

Thr
```

<210> SEQ ID NO 7
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Serine or threonine residue
<220> FEATURE:
<221> NAME/KEY: MOD_RES

```
<222> LOCATION: (1)..(1)
<223> OTHER INFORMATION: PHOSPHORYLATION
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Serine or threonine residue
<220> FEATURE:
<221> NAME/KEY: MOD_RES
<222> LOCATION: (5)..(5)
<223> OTHER INFORMATION: PHOSPHORYLATION

<400> SEQUENCE: 7

Xaa Xaa Xaa Xaa Xaa
1               5

<210> SEQ ID NO 8
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa is any amino acid residue excepting a
      glutamic acid residue

<400> SEQUENCE: 8

Lys Glu Xaa Pro Pro
1               5

<210> SEQ ID NO 9
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: PHOSPHORYLATION

<400> SEQUENCE: 9

Lys Glu Ala Pro Pro Ser Pro Pro Gln Ser Pro
1               5                   10

<210> SEQ ID NO 10
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' Myristilated peptide
<220> FEATURE:
<221> NAME/KEY: MOD_RES
<222> LOCATION: (11)..(11)
<223> OTHER INFORMATION: PHOSPHORYLATION

<400> SEQUENCE: 10

Gly Lys Glu Ala Pro Pro Ser Pro Pro Gln Ser Pro
1               5                   10

<210> SEQ ID NO 11
<211> LENGTH: 5
```

```
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 11

Ser Pro Pro Pro Ser
1               5

<210> SEQ ID NO 12
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 12

Ser Pro Pro Pro Thr
1               5

<210> SEQ ID NO 13
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 13

Ser Ala Pro Pro Ser
1               5

<210> SEQ ID NO 14
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 14

Ser Ala Pro Pro Thr
1               5

<210> SEQ ID NO 15
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 15
```

Ser Ala Ala Pro Ser
1               5

<210> SEQ ID NO 16
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 16

Ser Ala Ala Pro Thr
1               5

<210> SEQ ID NO 17
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 17

Ser Pro Ala Pro Ser
1               5

<210> SEQ ID NO 18
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 18

Ser Pro Ala Pro Thr
1               5

<210> SEQ ID NO 19
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 19

Ser Gly Pro Pro Ser
1               5

<210> SEQ ID NO 20
<211> LENGTH: 5
<212> TYPE: PRT
<213> ORGANISM: Artificial sequence
<220> FEATURE:
<223> OTHER INFORMATION: Synthetic peptide
<220> FEATURE:

```
<221> NAME/KEY: MOD_RES
<222> LOCATION: (5)..(5)
<223> OTHER INFORMATION: PHOSPHORYLATION

<400> SEQUENCE: 20

Ser Gly Pro Pro Thr
1               5

<210> SEQ ID NO 21
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 21

Ser Gly Gly Pro Ser
1               5

<210> SEQ ID NO 22
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 22

Ser Gly Gly Pro Thr
1               5

<210> SEQ ID NO 23
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 23

Ser Pro Gly Pro Ser
1               5

<210> SEQ ID NO 24
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 24

Ser Pro Gly Pro Thr
1               5

<210> SEQ ID NO 25
```

```
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Ile or Leu
<220> FEATURE:
<221> NAME/KEY: MOD_RES
<222> LOCATION: (5)..(5)
<223> OTHER INFORMATION: PHOSPHORYLATION

<400> SEQUENCE: 25

Ser Xaa Pro Pro Ser
1               5

<210> SEQ ID NO 26
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Ile or Leu
<220> FEATURE:
<221> NAME/KEY: MOD_RES
<222> LOCATION: (5)..(5)
<223> OTHER INFORMATION: PHOSPHORYLATION

<400> SEQUENCE: 26

Ser Xaa Pro Pro Thr
1               5

<210> SEQ ID NO 27
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Ile or Leu
<220> FEATURE:
<221> NAME/KEY: MOD_RES
<222> LOCATION: (5)..(5)
<223> OTHER INFORMATION: PHOSPHORYLATION

<400> SEQUENCE: 27

Ser Xaa Xaa Pro Ser
1               5

<210> SEQ ID NO 28
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Ile or Leu
<220> FEATURE:
<221> NAME/KEY: MOD_RES
<222> LOCATION: (5)..(5)
<223> OTHER INFORMATION: PHOSPHORYLATION

<400> SEQUENCE: 28
```

```
Ser Xaa Xaa Pro Thr
1               5

<210> SEQ ID NO 29
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Ile or Leu
<220> FEATURE:
<221> NAME/KEY: MOD_RES
<222> LOCATION: (5)..(5)
<223> OTHER INFORMATION: PHOSPHORYLATION

<400> SEQUENCE: 29

Ser Pro Xaa Pro Ser
1               5

<210> SEQ ID NO 30
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Ile or Leu
<220> FEATURE:
<221> NAME/KEY: MOD_RES
<222> LOCATION: (5)..(5)
<223> OTHER INFORMATION: PHOSPHORYLATION

<400> SEQUENCE: 30

Ser Pro Xaa Pro Thr
1               5

<210> SEQ ID NO 31
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 31

Ser Val Pro Pro Ser
1               5

<210> SEQ ID NO 32
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 32

Ser Val Pro Pro Thr
1               5
```

```
<210> SEQ ID NO 33
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 33

Ser Val Val Pro Ser
1               5

<210> SEQ ID NO 34
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 34

Ser Val Val Pro Thr
1               5

<210> SEQ ID NO 35
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 35

Ser Pro Val Pro Ser
1               5

<210> SEQ ID NO 36
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: PHOSPHORYLATION

<400> SEQUENCE: 36

Ser Pro Val Pro Thr
1               5

<210> SEQ ID NO 37
<211> LENGTH: 5
<212> TYPE: PRT
<213> ORGANISM: Artificial sequence
<220> FEATURE:
<223> OTHER INFORMATION: Synthetic peptide

<400> SEQUENCE: 37

Lys Glu Ala Pro Pro
```

```
1               5

<210> SEQ ID NO 38
<211> LENGTH: 5
<212> TYPE: PRT
<213> ORGANISM: Artificial sequence
<220> FEATURE:
<223> OTHER INFORMATION: Synthetic peptide

<400> SEQUENCE: 38

Lys Glu Gly Pro Pro
1               5

<210> SEQ ID NO 39
<211> LENGTH: 5
<212> TYPE: PRT
<213> ORGANISM: Artificial sequence
<220> FEATURE:
<223> OTHER INFORMATION: Synthetic peptide

<400> SEQUENCE: 39

Lys Glu Ile Pro Pro
1               5

<210> SEQ ID NO 40
<211> LENGTH: 5
<212> TYPE: PRT
<213> ORGANISM: Artificial sequence
<220> FEATURE:
<223> OTHER INFORMATION: Synthetic peptide

<400> SEQUENCE: 40

Lys Glu Leu Pro Pro
1               5

<210> SEQ ID NO 41
<211> LENGTH: 5
<212> TYPE: PRT
<213> ORGANISM: Artificial sequence
<220> FEATURE:
<223> OTHER INFORMATION: Synthetic peptide

<400> SEQUENCE: 41

Lys Glu Val Pro Pro
1               5

<210> SEQ ID NO 42
<211> LENGTH: 5
<212> TYPE: PRT
<213> ORGANISM: Artificial sequence
<220> FEATURE:
<223> OTHER INFORMATION: Synthetic peptide

<400> SEQUENCE: 42

Lys Glu Phe Pro Pro
1               5

<210> SEQ ID NO 43
<211> LENGTH: 12
<212> TYPE: PRT
<213> ORGANISM: Artificial sequence
<220> FEATURE:
<223> OTHER INFORMATION: L803-mts
<220> FEATURE:
<221> NAME/KEY: MOD_RES
<222> LOCATION: (1)..(1)
<223> OTHER INFORMATION: N' Myristilated peptide
<220> FEATURE:
```

```
<221> NAME/KEY: MOD_RES
<222> LOCATION: (11)..(11)
<223> OTHER INFORMATION: PHOSPHORYLATION

<400> SEQUENCE: 43

Gly Lys Glu Ala Pro Pro Ala Pro Pro Gln Ser Pro
1               5                   10

<210> SEQ ID NO 44
<211> LENGTH: 11
<212> TYPE: PRT
<213> ORGANISM: Artificial sequence
<220> FEATURE:
<223> OTHER INFORMATION: Phosphorylated L807 peptide
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION

<400> SEQUENCE: 44

Lys Glu Ala Pro Pro Ser Pro Pro Gln Ser Pro
1               5                   10

<210> SEQ ID NO 45
<211> LENGTH: 24
<212> TYPE: PRT
<213> ORGANISM: Artificial sequence
<220> FEATURE:
<223> OTHER INFORMATION: Exemplary GSK-3 substrate phosphorylation motif
      (Glycogen synthase)

<400> SEQUENCE: 45

Arg Pro Ala Ser Val Pro Pro Ser Pro Ser Leu Ser Arg His Ser Ser
1               5                   10                  15

Pro His Gln Ser Glu Asp Glu Glu
            20

<210> SEQ ID NO 46
<211> LENGTH: 13
<212> TYPE: PRT
<213> ORGANISM: Artificial sequence
<220> FEATURE:
<223> OTHER INFORMATION: Exemplary GSK-3 substrate phosphorylation motif
      (CREB)

<400> SEQUENCE: 46

Lys Arg Arg Glu Ile Leu Ser Arg Arg Pro Ser Tyr Arg
1               5                   10

<210> SEQ ID NO 47
<211> LENGTH: 13
<212> TYPE: PRT
<213> ORGANISM: Artificial sequence
<220> FEATURE:
<223> OTHER INFORMATION: Exemplary GSK-3 substrate phosphorylation motif
      (IRS1)

<400> SEQUENCE: 47

Glu Gly Thr Met Ser Arg Pro Ala Ser Val Asp Gly Ser
1               5                   10

<210> SEQ ID NO 48
<211> LENGTH: 15
<212> TYPE: PRT
```

<213> ORGANISM: Artificial sequence
<220> FEATURE:
<223> OTHER INFORMATION: Exemplary GSK-3 substrate phosphorylation motif (IRS2)

<400> SEQUENCE: 48

Ser Gly Ser Ala Ser Ala Ser Gly Ser Pro Ser Asp Pro Gly Phe
1               5                   10                  15

<210> SEQ ID NO 49
<211> LENGTH: 22
<212> TYPE: PRT
<213> ORGANISM: Artificial sequence
<220> FEATURE:
<223> OTHER INFORMATION: Exemplary GSK-3 substrate phosphorylation motif (beta-catenin)

<400> SEQUENCE: 49

Ser Tyr Leu Asp Ser Gly Ile His Ser Gly Ala Thr Thr Thr Ala Pro
1               5                   10                  15

Ser Leu Ser Gly Lys Gly
            20

<210> SEQ ID NO 50
<211> LENGTH: 16
<212> TYPE: PRT
<213> ORGANISM: Artificial sequence
<220> FEATURE:
<223> OTHER INFORMATION: Exemplary GSK-3 substrate phosphorylation motif (HSF1)

<400> SEQUENCE: 50

Glu Glu Pro Pro Ser Pro Pro Gln Ser Pro Arg Val Glu Glu Ala Ser
1               5                   10                  15

<210> SEQ ID NO 51
<211> LENGTH: 23
<212> TYPE: PRT
<213> ORGANISM: Artificial sequence
<220> FEATURE:
<223> OTHER INFORMATION: Exemplary GSK-3 substrate phosphorylation motif (ATP-citrate lyase)

<400> SEQUENCE: 51

Leu Leu Asn Ala Ser Gly Ser Thr Ser Thr Pro Ala Pro Ser Arg Thr
1               5                   10                  15

Ala Ser Phe Ser Glu Ser Arg
            20

<210> SEQ ID NO 52
<211> LENGTH: 23
<212> TYPE: PRT
<213> ORGANISM: Artificial sequence
<220> FEATURE:
<223> OTHER INFORMATION: Exemplary GSK-3 substrate phosphorylation motif (G subunit of phosphatase1)

<400> SEQUENCE: 52

Ala Ile Phe Lys Pro Gly Phe Ser Pro Gln Pro Ser Arg Arg Gly Ser
1               5                   10                  15

Glu Ser Ser Glu Glu Val Tyr
            20

<210> SEQ ID NO 53
<211> LENGTH: 20
<212> TYPE: PRT

```
<213> ORGANISM: Artificial sequence
<220> FEATURE:
<223> OTHER INFORMATION: Exemplary GSK-3 substrate phospohrylation motif
      (eIF2B)

<400> SEQUENCE: 53

Asp Ser Glu Glu Leu Asp Ser Arg Ala Gly Ser Pro Gln Leu Asp Asp
1               5                   10                  15

Ile Lys Val Phe
            20

<210> SEQ ID NO 54
<211> LENGTH: 23
<212> TYPE: PRT
<213> ORGANISM: Artificial sequence
<220> FEATURE:
<223> OTHER INFORMATION: Exemplary GSK-3 substrate phospohrylation motif
      (Inhibitor-2)

<400> SEQUENCE: 54

Gly Leu Met Lys Ile Asp Glu Pro Ser Thr Pro Tyr His Ser Met Ile
1               5                   10                  15

Gly Asp Asp Asp Asp Ala Tyr
            20

<210> SEQ ID NO 55
<211> LENGTH: 14
<212> TYPE: PRT
<213> ORGANISM: Artificial sequence
<220> FEATURE:
<223> OTHER INFORMATION: pIRS-1 an GSK-3beta exemplary substrate peptie
<220> FEATURE:
<221> NAME/KEY: MOD_RES
<222> LOCATION: (11)..(11)
<223> OTHER INFORMATION: PHOSPHORYLATION

<400> SEQUENCE: 55

Arg Arg Glu Gly Gly Met Ser Arg Pro Ala Ser Val Asp Gly
1               5                   10
```